(12) United States Patent
Parker et al.

(10) Patent No.: US 9,089,715 B2
(45) Date of Patent: *Jul. 28, 2015

(54) FORMING FEEDTHROUGHS FOR HERMETICALLY SEALED HOUSINGS USING TWO-MATERIAL POWDER INJECTION MOLDING

(75) Inventors: John L. Parker, Alexandria (AU); David Robinson, Alexandria (AU); David Thomas, Alexandria (AU); Mark Fretz, Alexandria (AU)

(73) Assignee: SALUDA MEDICAL PTY LIMITED, Eveleigh, NSW (AU)

( * ) Notice: Subject to any disclaimer, the term of this patent is extended or adjusted under 35 U.S.C. 154(b) by 458 days.

This patent is subject to a terminal disclaimer.

(21) Appl. No.: 13/512,172

(22) PCT Filed: Nov. 26, 2010

(86) PCT No.: PCT/US2010/058127
§ 371 (c)(1),
(2), (4) Date: Aug. 13, 2012

(87) PCT Pub. No.: WO2011/066478
PCT Pub. Date: Jun. 3, 2011

(65) Prior Publication Data
US 2012/0319319 A1    Dec. 20, 2012

(30) Foreign Application Priority Data
Nov. 26, 2009 (AU) .................. 2009905781

(51) Int. Cl.
*B29C 45/16* (2006.01)
*A61N 1/375* (2006.01)
(Continued)

(52) U.S. Cl.
CPC ............. *A61N 1/3754* (2013.01); *A61N 1/3756* (2013.01); *B22F 3/225* (2013.01);
(Continued)

(58) Field of Classification Search
CPC .... B22F 3/225; B29C 33/302; B29C 45/0001
USPC ......................................................... 264/104
See application file for complete search history.

(56) References Cited

U.S. PATENT DOCUMENTS 5,183,096 A    2/1993   Cook
5,657,811 A    8/1997   Cook
(Continued)

FOREIGN PATENT DOCUMENTS

WO    2009/009827    1/2009
WO    2009/015438    2/2009

OTHER PUBLICATIONS

International Search Report, PCT/US2010/058127, completion date Jan. 16, 2011, 4 pages.
(Continued)

*Primary Examiner* — Alison Hindenlang
*Assistant Examiner* — Robert J Grun

(57) ABSTRACT

Methods of forming a feedthrough using a mold that defines a cavity when closed and includes one or more cores configured to move in and out of the mold cavity. The methods include injecting non-electrically conductive powder injection molding (PIM) feedstock into the mold cavity to form an insulative body around a portion of each of the cores disposed in the mold cavity, removing each of the cores from the insulative body to form one or more core cavities in the insulative body, injecting electrically conductive PIM feedstock into the core cavities to form one or more conductors in the core cavities, respectively, and sintering the insulative body and the conductors to form the feedthrough.

20 Claims, 19 Drawing Sheets

(51) Int. Cl.
*C04B 111/00* (2006.01)
*B28B 1/24* (2006.01)
*B29C 33/30* (2006.01)
*B22F 3/22* (2006.01)
*B29C 45/00* (2006.01)

(52) U.S. Cl.
CPC ............... *B28B 1/24* (2013.01); *B29C 33/302* (2013.01); *B29C 45/0001* (2013.01); *C04B 2111/00137* (2013.01); *C04B 2235/6022* (2013.01)

(56) References Cited

U.S. PATENT DOCUMENTS

| | | | |
|---|---|---|---|
| 6,010,803 | A | 1/2000 | Heller, Jr. et al. |
| 2004/0232597 | A1 | 11/2004 | Sjostedt et al. |
| 2006/0141861 | A1 | 6/2006 | Darley et al. |
| 2007/0063336 | A1 | 3/2007 | Hase |
| 2007/0183118 | A1 | 8/2007 | Fu et al. |
| 2008/0208289 | A1 | 8/2008 | Darley et al. |

OTHER PUBLICATIONS

European Search Report, Appl. No. 10833993.8, issue date Apr. 17, 2013; 8 pages.

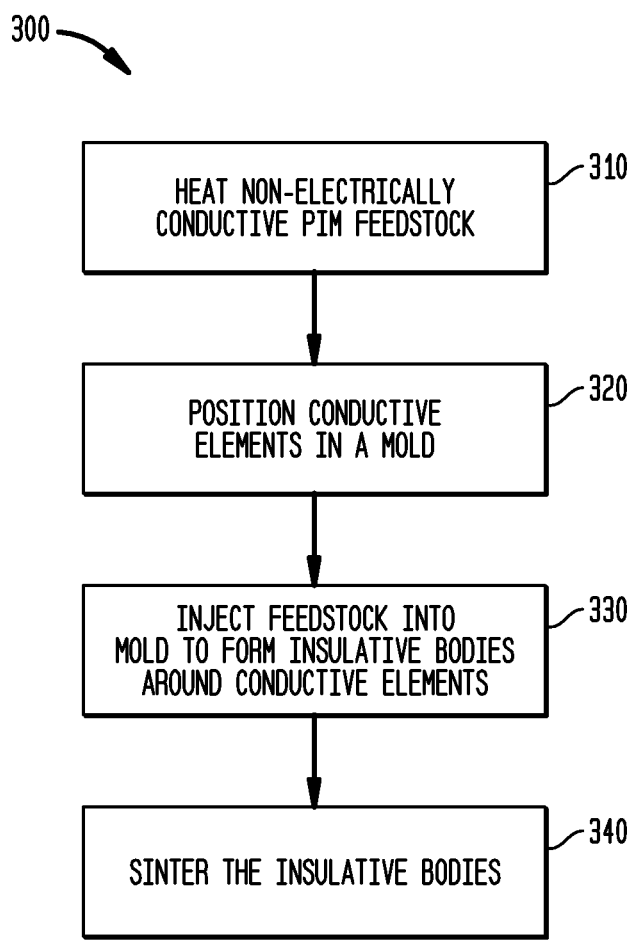

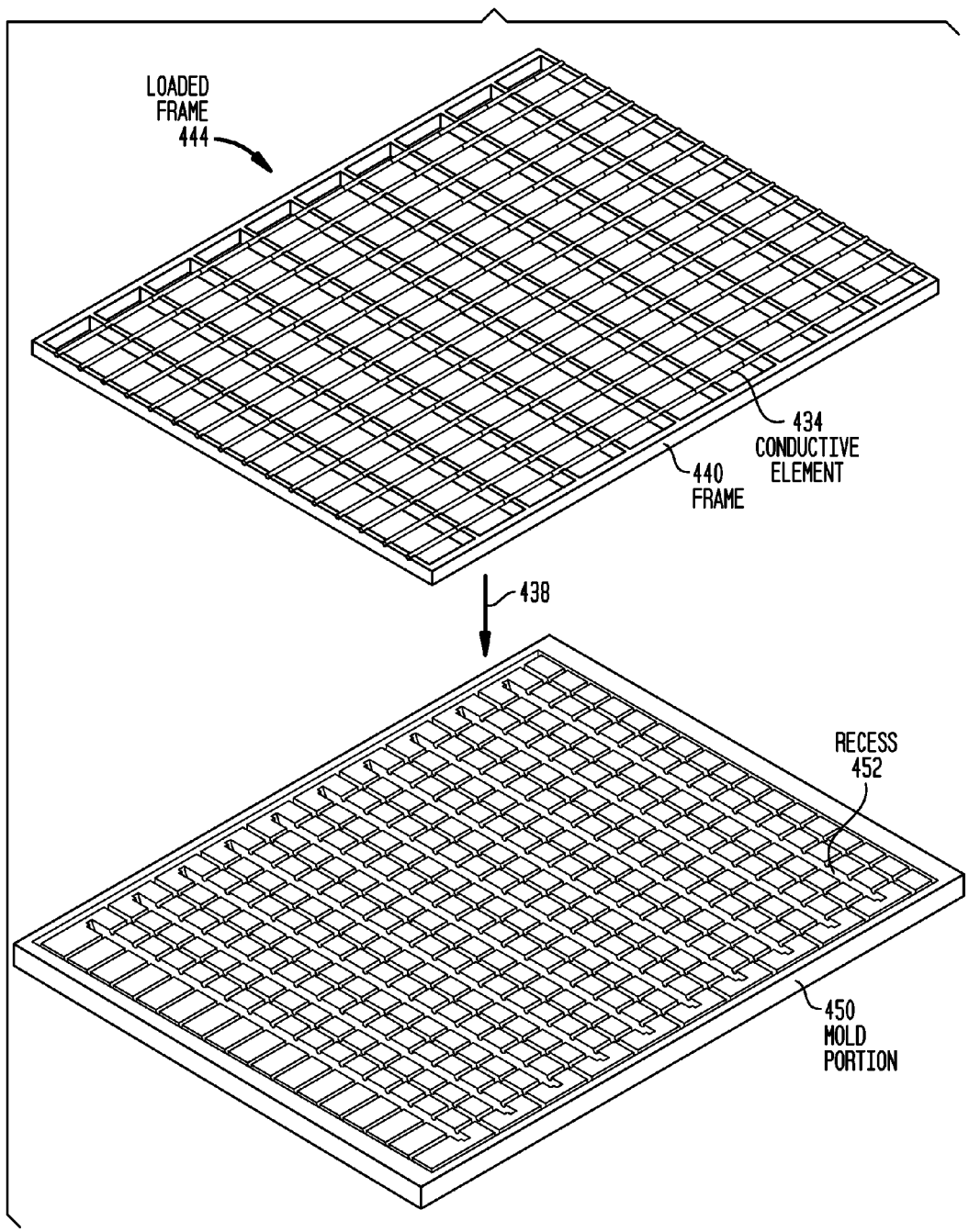

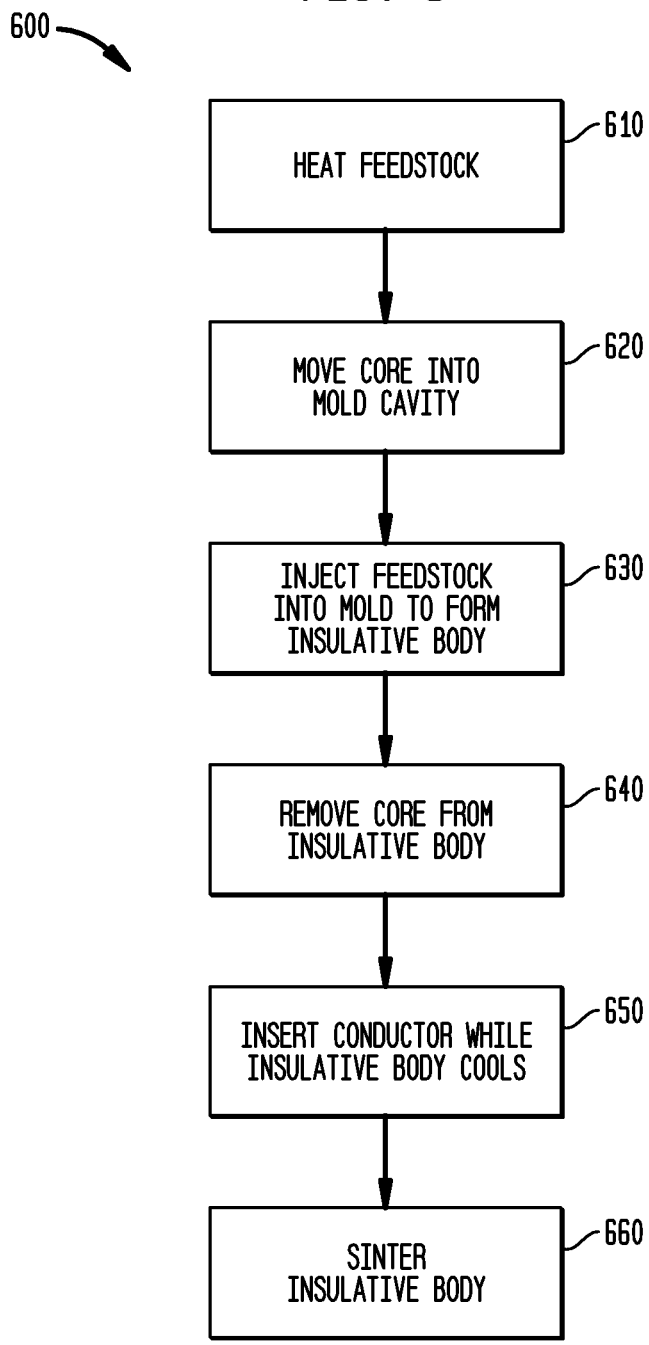

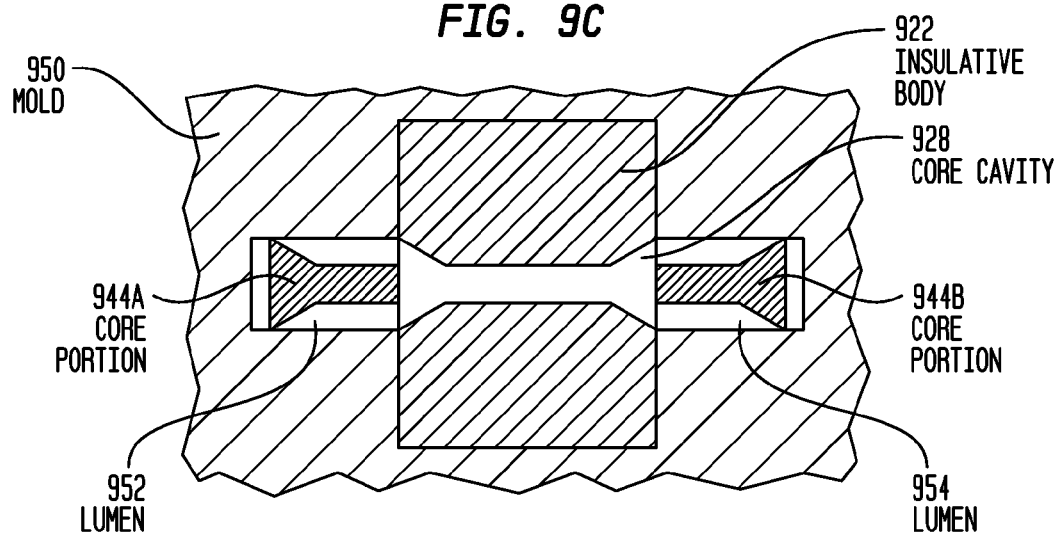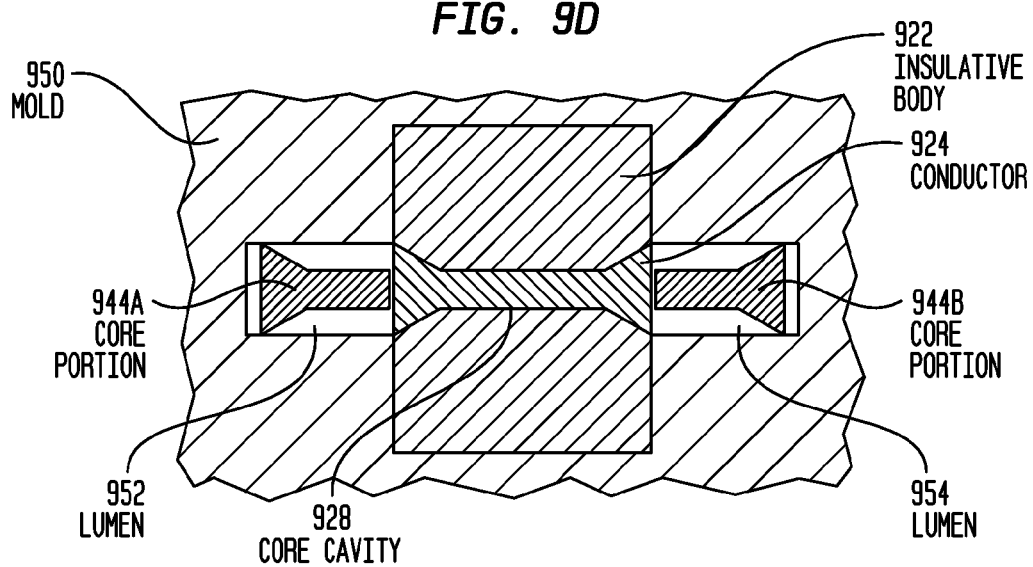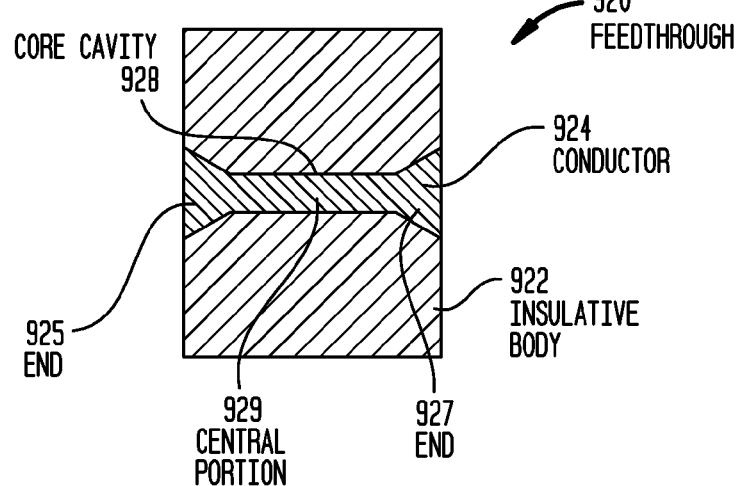

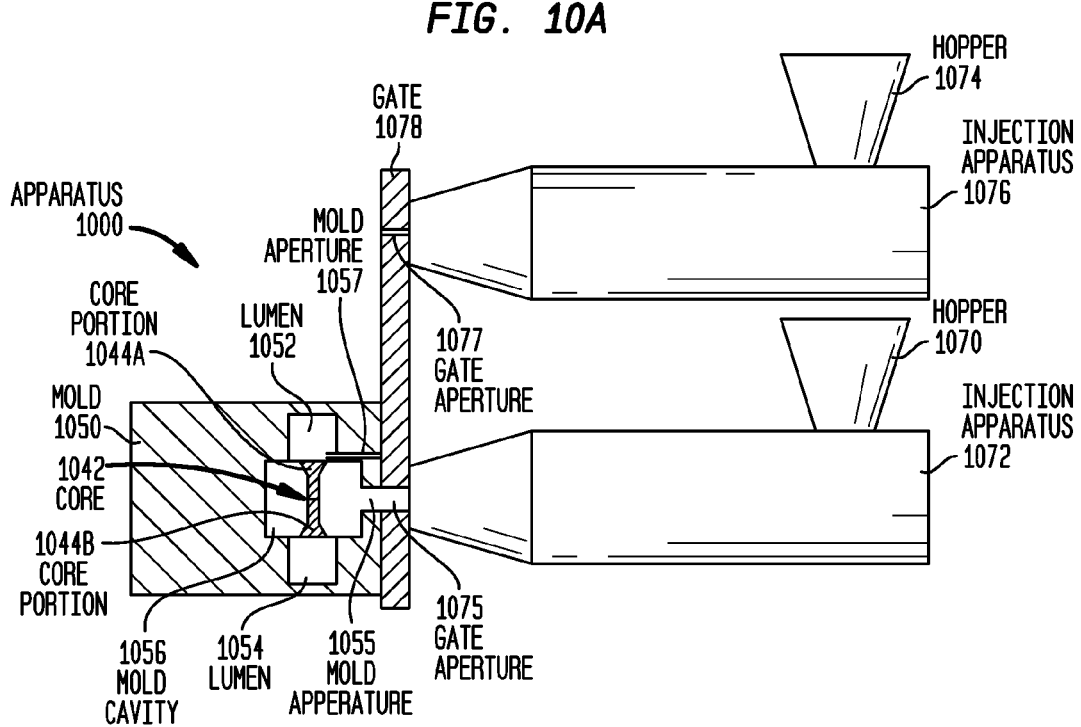
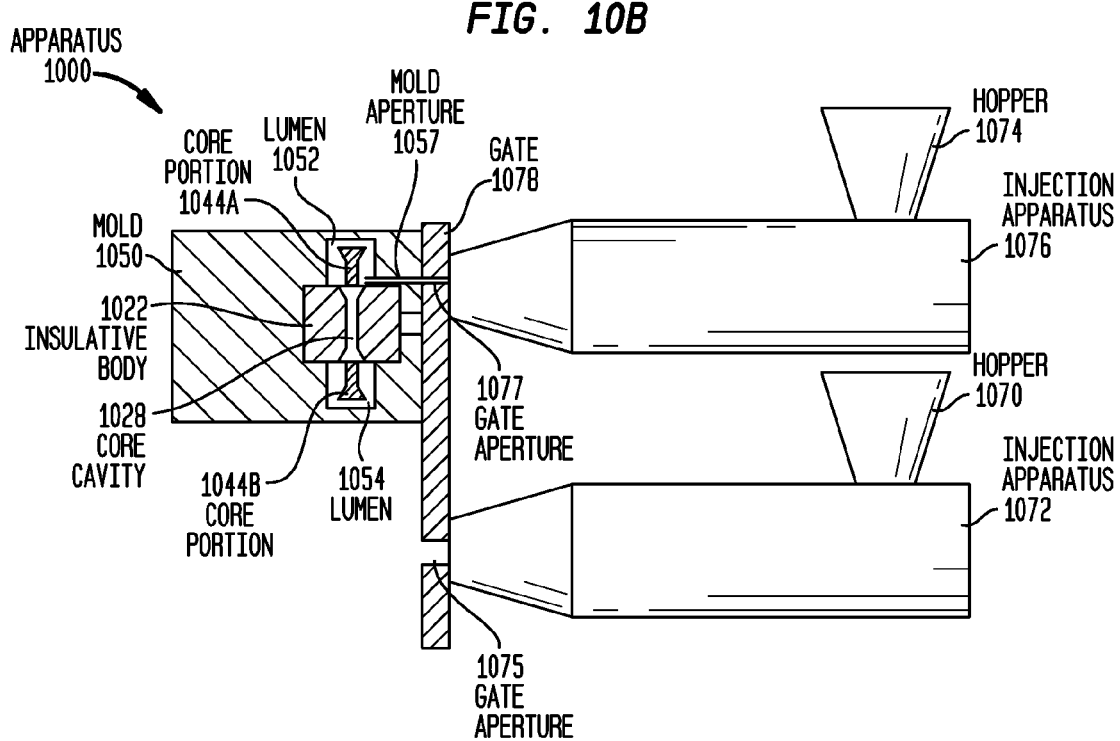

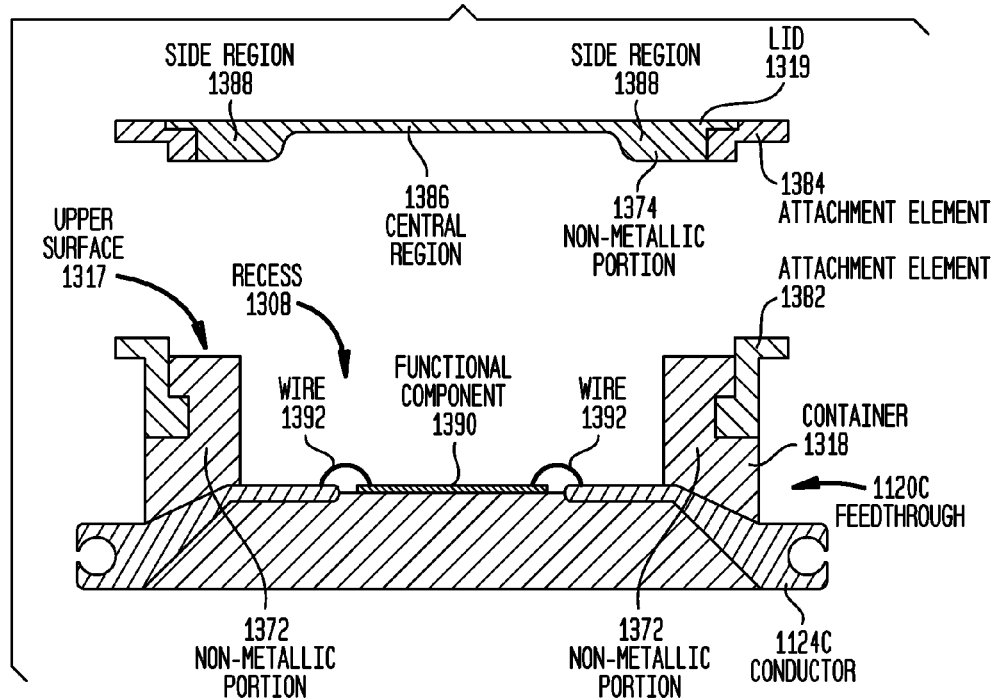
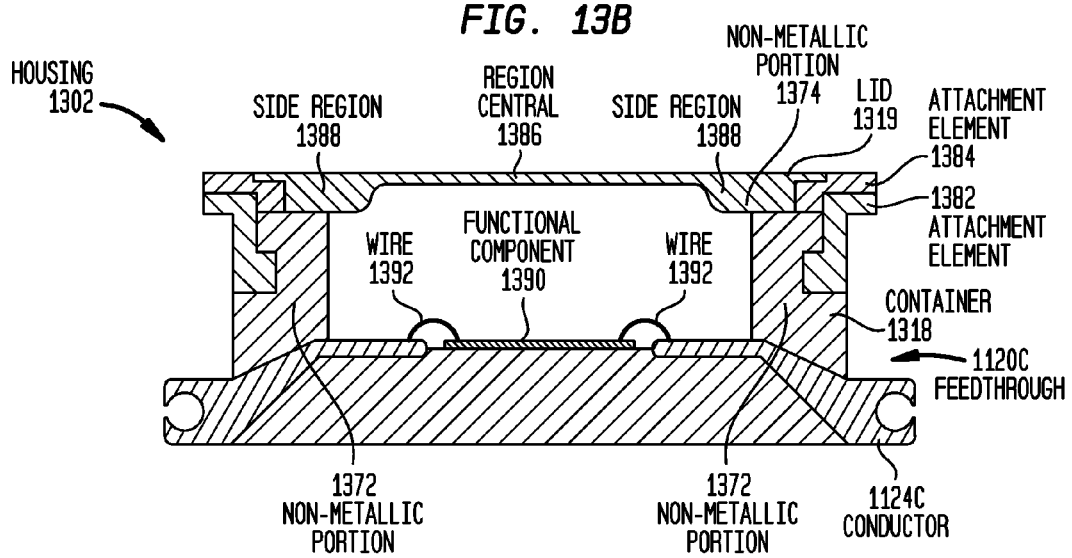

FORMING FEEDTHROUGHS FOR HERMETICALLY SEALED HOUSINGS USING TWO-MATERIAL POWDER INJECTION MOLDING

CROSS-REFERENCE TO RELATED APPLICATIONS

The present application claims the benefit of Australian Provisional Patent Application No. 2009905781, filed Nov. 26, 2009, which is hereby incorporated by reference herein.

BACKGROUND

1. Field of the Invention

The present invention generally relates to methods for forming feedthroughs for hermetically sealed housings, and more particularly, to methods for forming feedthroughs for hermetically sealed housings using two-material powder injection molding (PIM).

2. Related Art

An insulative element having one or more electrically conductive paths extending from one side of the insulative element to another is generally referred to herein as a "feedthrough." In some applications, feedthroughs may be used to provide an electrically conductive path through an insulative element. For example, feedthroughs are often used to provide electrically conductive path(s) through a non-electrically conductive portion of a housing to electrically connect one or more components external the housing to components internal the housing.

Feedthroughs for hermetically sealed housings are often utilized in medical devices having one or more active implantable components, generally referred to herein as active implantable medical devices (AIMDs). Such feedthroughs provide one or more conductive paths through an insulative element while maintaining the hermetic integrity of the housing. AIMDs often include an implantable, bio-compatible, hermetically sealed electronics module, and a component that interfaces with a patient's tissue. The tissue interface component may include, for example, one or more instruments, apparatus, sensors or other active or passive components that are permanently or temporarily implanted in a patient. The tissue interface component is used to, for example, diagnose, monitor, and/or treat a disease or injury, or to modify a patient's anatomy or physiological process.

In particular applications, an AIMD tissue interface includes one or more electrical contacts, referred to as electrodes, which deliver electrical stimulation signals to, or receive signals from, a patient's tissue. The electrodes are typically disposed in a biocompatible carrier member, and are electrically connected to the electronics module. The electrodes and the non-conductive member are collectively referred to herein as an electrode assembly.

SUMMARY

In one aspect of the invention, a method of forming a feedthrough is disclosed. The method uses a mold that defines a cavity when closed and includes one or more cores configured to move in and out of the mold cavity. The method comprises injecting non-electrically conductive powder injection molding (PIM) feedstock into the mold cavity to form an insulative body around a portion of each of the cores disposed in the mold cavity, removing each of the cores from the insulative body to form one or more core cavities in the insulative body, injecting electrically conductive PIM feedstock into the core cavities to form one or more conductors in the core cavities, respectively, and sintering the insulative body and the conductors to form the feedthrough.

In another aspect of the invention, a method of forming an implantable device comprising a feedthrough is disclosed. The method uses a mold that defines a cavity when closed and includes one or more cores configured to move in and out of the mold cavity. The method comprises injecting non-electrically conductive powder injection molding (PIM) feedstock into the mold cavity to form a container at least partially around the cores disposed in the mold cavity, removing the cores from the container to form one or more core cavities, and injecting electrically conductive PIM feedstock into the core cavities to form one or more conductors in the core cavities, respectively, each conductor having a first end exposed in a recess of the container and a second end exposed adjacent an outer surface of the container. The method further comprises sintering the container and the conductors, and hermetically sealing a lid to the container to form a first housing.

In yet another aspect of the invention, a method of forming a hermetically sealed housing comprising a feedthrough is disclosed. The method uses a mold that defines a first mold cavity when closed and includes a plurality of first cores configured to move in and out of the first mold cavity. The method comprises injecting non-electrically conductive powder injection molding (PIM) feedstock into the first mold cavity to form a first insulative body at least partially around the first cores disposed in the first mold cavity, removing the first cores from the first mold cavity to form a plurality of first core cavities each disposed in or adjacent to the first insulative body, and injecting the heated, electrically conductive metallic PIM feedstock into the first core cavities to form a first container having one or more conductors and one or more first metallic attachment elements, wherein each of the one or more conductors has a first end exposed in a recess of the first insulative body and a second end exposed adjacent an outer surface of the first insulative body. The method further comprises sintering the container, and joining one or more second metallic attachment elements of a lid to the first metallic attachment elements, respectively, to form a hermetically sealed housing.

BRIEF DESCRIPTION OF THE DRAWINGS

Illustrative embodiments of the present invention are described herein with reference to the accompanying drawings, in which:

FIG. 3 is a flowchart illustrating a method of forming a plurality of feedthroughs in accordance with embodiments of the present invention;

FIG. 4C illustrates a portion of a mold configured to receive a frame comprising conductive elements positioned on the frame, in accordance with embodiments of the present invention;

FIG. 6 is a flowchart illustrating a method of forming a feedthrough in accordance with embodiments of the present invention;

FIGS. 9A-9E are cross-sectional views illustrating the formation of a feedthrough using a mold in accordance with embodiments of the method illustrated in FIG. 8;

FIGS. 10A and 10B schematically illustrate an injection molding apparatus that may be used to perform two-material PIM in accordance with embodiments of the present invention;

FIGS. 13A and 13B are cross-sectional views of a housing with feedthroughs that may be formed in accordance with embodiments of the present invention.

DETAILED DESCRIPTION

Aspects of the present invention are generally directed to methods for forming feedthroughs for hermetically sealed housings using powder injection molding (PIM). In accordance with embodiments of the present invention, the PIM may be used to form an insulative body around one or more conductors. In other embodiments, a two-material PIM process may be used to form both an insulative body and conductors extending through the insulative body to form a feedthrough. Advantageously, embodiments of the present invention provide methods for forming a feedthrough without the need for a sacrificial conductive components, thereby eliminating the cost and waste associated with such sacrificial components.

Figure 1:
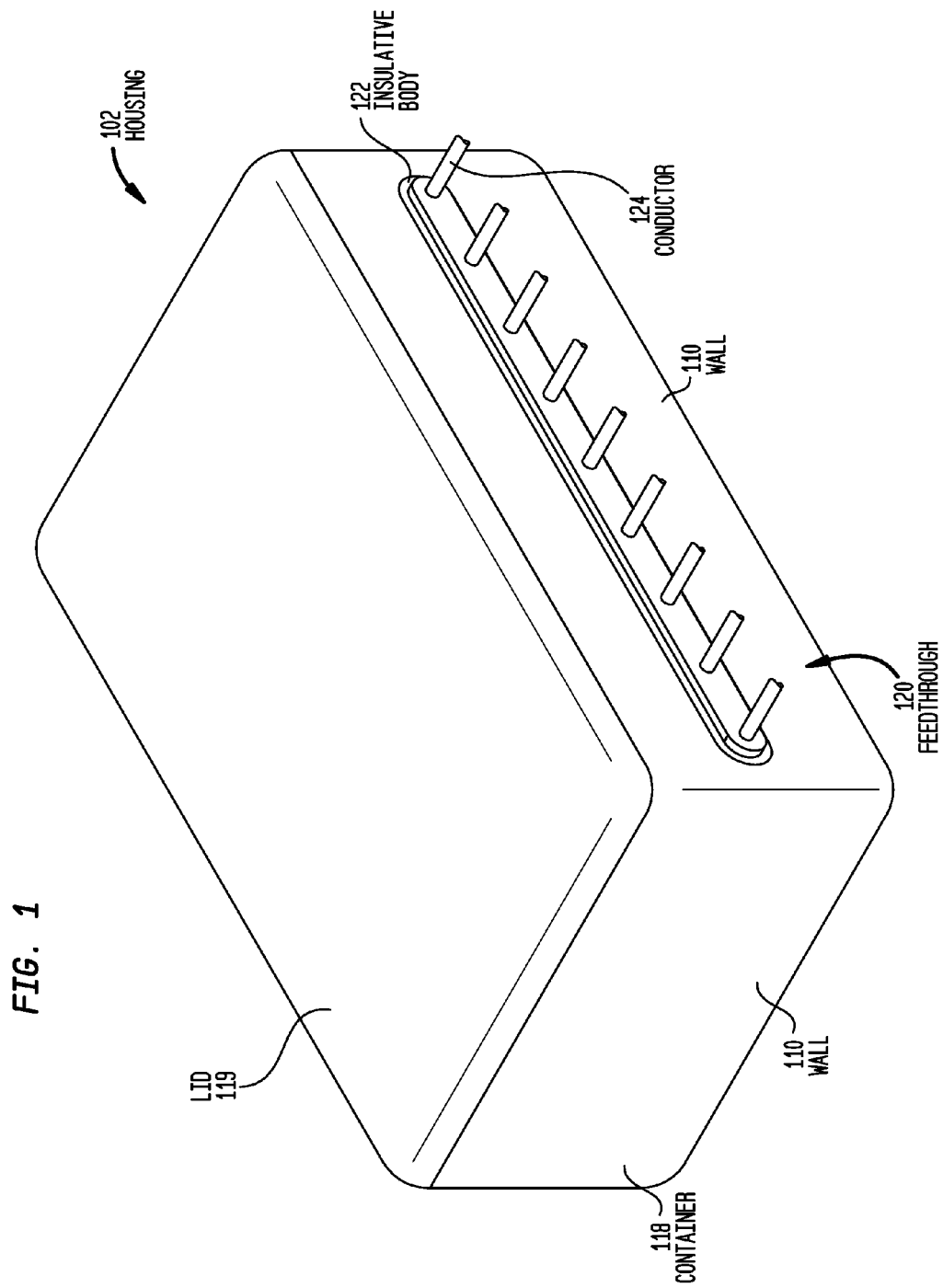
FIG. 1 is a perspective view of an exemplary hermetically sealed housing including a feedthrough that may be formed in accordance with embodiments of the present invention.

FIG. 1 is a perspective view of an exemplary hermetically sealed housing 102 including a feedthrough 120 that may be formed in accordance with embodiments of the present invention. In the embodiment illustrated in FIG. 1, housing 102 comprises a container 118 and a lid 119 hermetically sealed to container 118. As used herein, a "container" is any structure that contains or can contain or receive any component or element, and which interoperates with another structure to form a hermetically sealed housing enclosing the component or element. As shown in FIG. 1, container 118 comprises a plurality of walls 110. Housing 102 further includes an inner recess (not shown) defined by walls 110 in which various components can be contained. For example, in embodiments in which housing 102 is a component of an AIMD, the inner recess may contain one or more functional components. As used herein, a "functional component" is any type of electronic component utilized in a housing in conjunction with and/or independently of one or more electronic components external the housing. In embodiments, walls 110 and lid 119 are electrically insulative.

As shown in FIG. 1, housing 102 also comprises a feedthrough 120 disposed in one of walls 110. In other embodiments, multiple feedthroughs 120 may be disposed in multiple walls 110. In the embodiment shown in FIG. 1, feedthrough 120 is integrated into wall 110 such that a hermetic seal is formed between wall 110 and feedthrough 120. Feedthrough 120 includes an insulative body 122 and conductors 124 extending from one side of insulative body 122 to another. In embodiments, conductors 124 provide respective conductive paths for connecting one or more functional components located inside housing 102 with one or more components disposed outside of housing 102. For example, conductors 124 may be electrically connected to a tissue interface or to conductors of a feedthrough of another housing in embodiments of the present invention.

In accordance with embodiments of the present invention, the insulative body of a feedthrough may form a portion of one or more housing walls, an entire wall of a housing, or form multiple walls of a housing. In the embodiment shown in FIG. 1, for example, insualtive body 122 is integrated into and forms a portion of a wall 110. In alternative embodiments, a feedthrough may comprise conductors 124 extending from one side of an insulative wall 110 of housing 102 to another side of the wall 110, such that the insulative body is unitary with the insulative wall 110. In such embodiments, there is no separate insulative body integrated into wall 110. Additionally, while feedthrough 120 shown in FIG. 1A includes nine conductors, this number of conductors is merely exemplary. In embodiments of the present invention, a feedthrough may contain any number of conductors.

Figure 2:
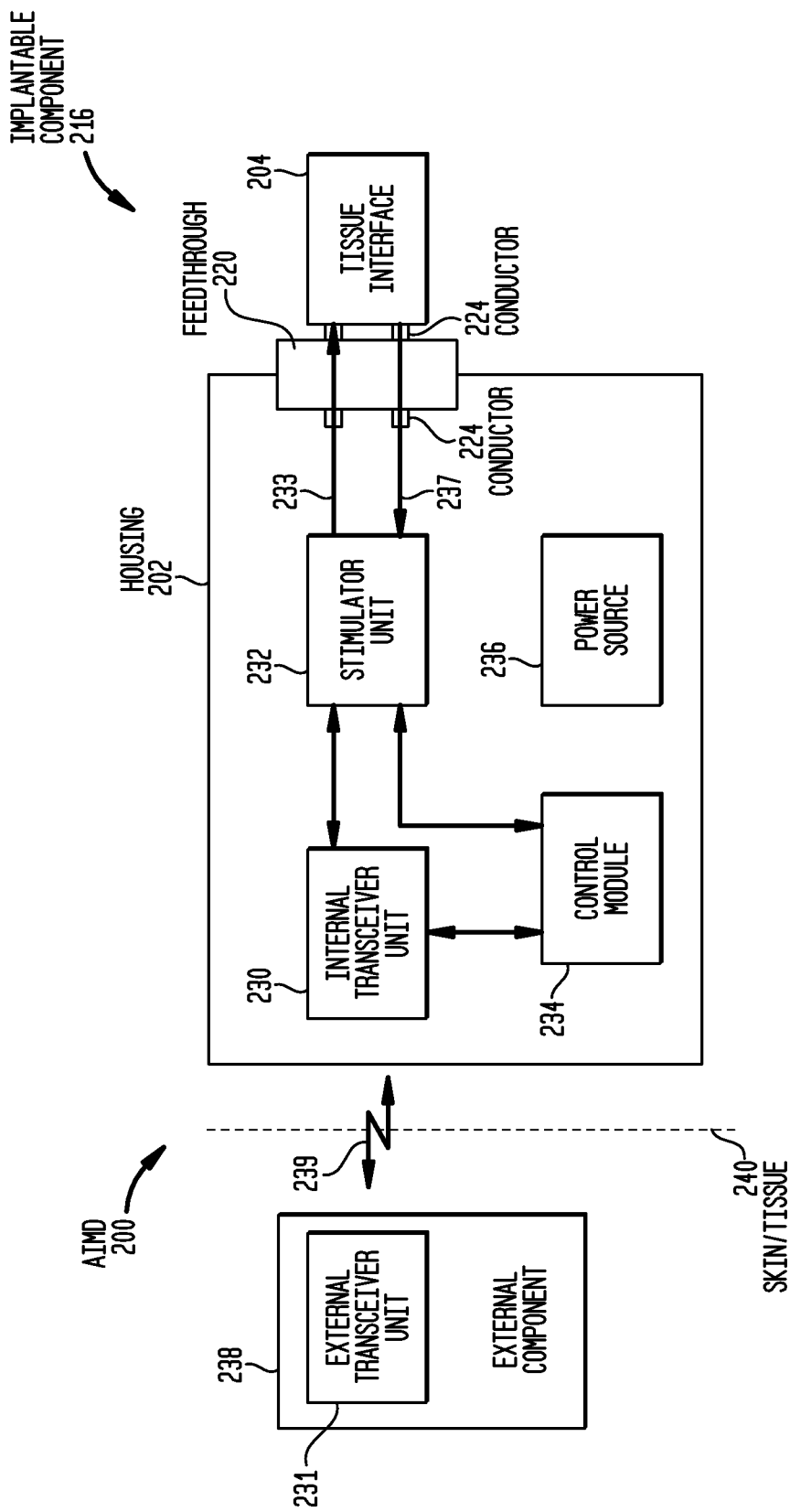
FIG. 2 is a functional block diagram illustrating an active implantable medical device (AIMD) in accordance with embodiments of the present invention.

FIG. 2 is a functional block diagram illustrating an active implantable medical device (AIMD) 200 in accordance with embodiments of the present invention. In the embodiment illustrated in FIG. 2, AIMD 200 comprises an implantable component 216 that includes an embodiment of housing 102 of FIG. 1, referred to herein as housing 202. Housing 202 (which may be referred to as an electronics module) is implanted under a patient's skin/tissue 240, cooperates with an external component 238, and contains various functional components. External component 238 comprises an external transceiver unit 231 that forms a bi-directional transcutaneous communication link 239 with an internal transceiver unit 230 disposed in housing 202. Transcutaneous communication link 239 may be used by external component 238 to transmit power and/or data to implantable component 216. Similarly, transcutaneous communication link 239 may be used by implantable component 216 to transmit data to external component 238.

In embodiments, transceiver units 230 and 231 each include a collection of one or more components configured to receive and/or transfer power and/or data. Transceiver units 230 and 231 may each comprise, for example, a coil for a magnetic inductive arrangement, a capacitive plate, or any other suitable arrangement. As such, in embodiments of the present invention, various types of transcutaneous communication, such as infrared (IR), electromagnetic, capacitive and inductive transfer may be used to transfer the power and/or data between external component 238 and implantable component 216.

In the embodiment shown in FIG. 2, housing 202 further includes a stimulator unit 232 that generates electrical stimulation signals 233. Electrical stimulation signals 233 are provided to a tissue interface 204 via one or more conductors 224 of feedthrough 220, which is an embodiment of feedthrough 220 illustrated in FIG. 2. In embodiments, tissue interface 204 includes electrodes that deliver electrical stimulation signals 233 to a patient's tissue. Stimulator unit 232 may generate electrical stimulation signals 233 based on, for example, data received from external component 238, signals received from a control module 234, in a pre-determined or pre-programmed pattern, etc. In certain embodiments, electrodes of tissue interface 204 are configured to receive signals from a patient's tissue. In such embodiments, signals 237 representing the recorded response may be provided to stimulator unit 232 via one or more conductors 224 of feedthrough 220 for forwarding to control module 234, or to external component 238 via transcutaneous communication link 239.

In the embodiment shown in FIG. 2, implantable component 216 is a totally implantable medical device that is capable of operating, at least for a period of time, without the need for external component 238. Therefore, implantable component 216 further comprises a rechargeable power source 236 in housing 216 that stores power received from external component 238. The power source may comprise, for example, a rechargeable battery. During operation of AIMD 200, the power stored by the power source is distributed to the various other components of implantable component 216 as needed. For ease of illustration, electrical connections between power source 236 and the other components in housing 202 have been omitted. FIG. 1B illustrates power source 236 located in housing 202, but in other embodiments the power source may be disposed in a separate implanted location. FIG. 2 illustrates specific embodiments of the present invention in which implantable component 216 cooperates with an external component 238. It should be appreciated that in alternative embodiments, AIMD 200 may be configured to operate entirely without the assistance of an external component.

FIG. 3 is a flowchart illustrating a method 300 of forming a plurality of feedthroughs in accordance with embodiments of the present invention. FIGS. 4A-4D illustrate elements used in or resulting from various aspects of the method illustrated in FIG. 3. For ease of explanation, the embodiments of FIG. 3 will be described with reference to the elements illustrated in FIGS. 4A-4D.

Figure 4A:
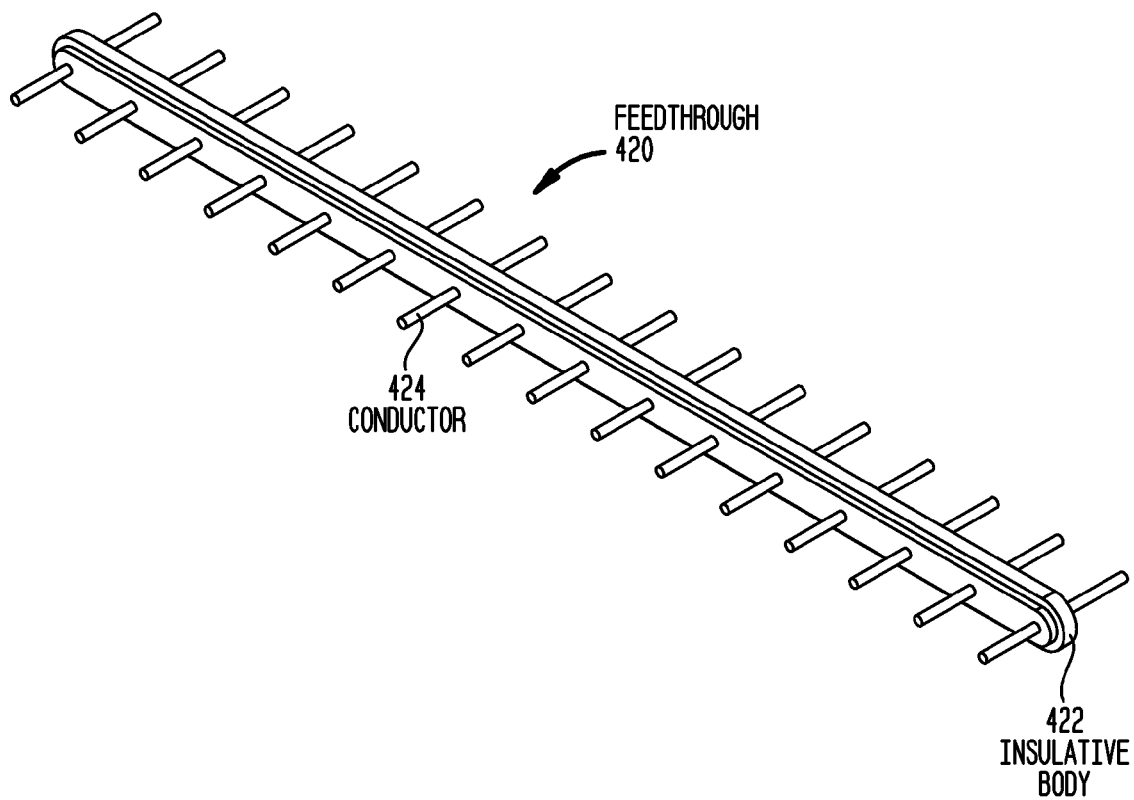
FIG. 4A is a perspective view of a feedthrough which may be formed in accordance with embodiments of the present invention.

FIG. 4A is a perspective view of an embodiment of feedthrough 120 (FIG. 1) which may be formed in accordance with embodiments of the present invention, and is referred to herein as feedthrough 420. Feedthrough 420 may be integrated into a wall of a hermetically sealed housing, such as housing 102 illustrated in FIG. 1, such that an interface between feedthrough 420 and the wall is hermetically sealed. As shown in FIG. 4A, feedthrough 420 includes an insulative body 422 and a plurality of conductors 424. Each conductor 424 passes through an insulative body 422 to extend from two sides of the body. Typically, the conductor 424 extends from opposing sides of an insulative body 422. In some embodiments, insulative body 422 is bio-compatible, electrically insulative and fluid impermeable. As described below, a plurality of feedthroughs 420 may be formed by the method illustrated in FIG. 3.

Method 300 illustrated in FIG. 3 is a method of forming a feedthrough using powder injection molding (PIM) fabrication techniques. PIM fabrication techniques, which include simple molding, insert molding, and two-color molding techniques, combine advantages of injection molding techniques, such as relatively low cost fabrication and net-shape component production, with the advantages provided by materials such as sintered ceramic and/or powdered metal materials. For information regarding recent advances in PIM fabrication techniques, see, for example, Petzoldt, "Micro Powder Injection Moulding—Challenges and Opportunities," PIM International, Vol. 2, No. 1, pgs. 37-42 (March 2008).

Method 300 illustrated in FIG. 3 begins at block 310 with heating a bio-compatible and non-electrically conductive PIM feedstock, which is the material that will be injected into a mold. As used herein, "feedstock" generally refers to the material that will be injected into a mold in an injection molding process. Feedstock used in PIM, which may be referred to herein as "PIM feedstock", includes at least one or more powders and one or more binding agents (e.g., polymeric binders). PIM feedstock may also include other additives such as one or more lubricants. The powder may be a powdered ceramic, such as aluminum oxide or zirconium oxide. PIM feedstock used to form a non-electrically conductive element is referred to herein as "non-electrically conductive PIM feedstock." A non-electrically conductive PIM feedstock may be formed from a mixture of a powdered ceramic, one or more binding agents, and one or more additives. PIM feedstock used to form an electrically conductive element is referred to herein as "electrically conductive PIM feedstock." Electrically conductive PIM feedstock may be produced by a mixture of materials used to create a non-electrically conductive PIM feedstock with an appropriate additive. For example, an electrically conductive PIM feedstock may be produced by mixing titanium nitride with the powdered ceramic, binding agents and additives (if any) used to produce a non-electrically conductive PIM feedstock.

Figure 4B:
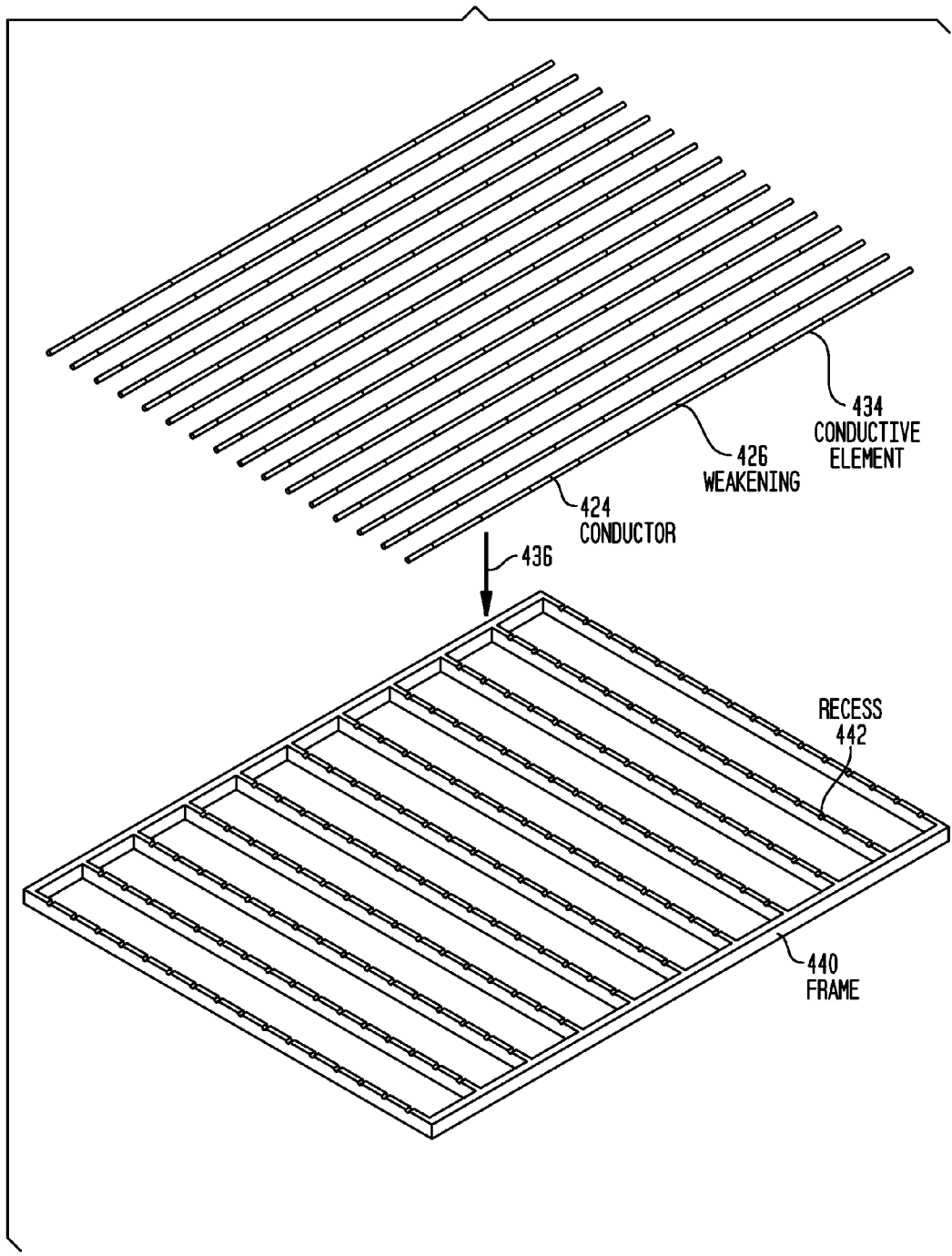
FIG. 4B illustrates a plurality of physically separate conductive elements and a frame configured to receive the conductive elements, in accordance with embodiments of the present invention.

At block 310, the PIM feedstock is heated to a temperature sufficient to cause the binding agents of the PIM feedstock to enter a liquid phase so that the PIM feedstock can flow and thus may be injected into a mold. At block 320, a plurality of separate conductive elements 434 are positioned in a mold. In certain embodiments, conductive elements 434 are positioned in the mold after heating the PIM feedstock is heated. In alternative embodiments, conductive elements 434 may be positioned in the mold before the PIM feedstock is heated or while the feedstock is being heated. Positioning conductive elements 434 in a mold in accordance with embodiments of the invention is shown in FIGS. 4B and 4C. In the embodiment illustrated in FIGS. 4A-4D, conductive elements 434 are positioned in a mold by first placing the conductive elements in a frame configured to hold conductive elements 434 in a desired configuration for placement in a mold. The frame holding conductive elements 434 is placed in the mold so that the conductive elements are positioned in the mold in the desired configuration.

FIG. 4B illustrates a plurality of physically separate conductive elements 434 and a frame 440 configured to receive conductive elements 434, in accordance with embodiments of the present invention. In the embodiment illustrated in FIGS. 4A-4D, each conductive element 434 is a contiguous length of electrically conductive material. Each conductive element 434 may be cut or otherwise severed to form a plurality of physically separate conductors 424. In embodiments of the present invention, each conductive element 434 has one or more locations at which the conductive element 434 is severed into conductors 424. In some embodiments, each conductive element 434 includes one or more structural weaknesses 426 at these locations to facilitate the severing of conductive element 434 into conductors 424. Structural weaknesses 426 may be implemented as perforations, reduced dimensions, regions formed from weaker materials than other regions of element 434, etc. In other embodiments, each conductive element 434 may include markings at the locations at which the conductive element 434 may be severed. In still other embodiments, each conductive element 434 is a uniform conductor with no structural difference or markings at the locations at which the conductive element 434 may be severed.

Frame 440 is configured to receive and support conductive elements 434. As shown in FIG. 4B, frame 440 includes recesses 442 configured to receive and support conductive elements 434 in a desired orientation relative to one another. In embodiments of method 300, conductive elements 434 may be lowered onto frame 440 in the direction of arrow 436 to form a loaded frame 444 (FIG. 4C). A frame onto which conductive elements have been lowered may be referred to herein as a "loaded frame." In specific embodiments, conductive elements 434 may be lowered onto frame 440 simultaneously or at different times.

FIG. 4C illustrates a first portion 450 of a mold configured to receive a frame 440 comprising conductive elements 434 positioned on frame 440, in accordance with embodiments of the present invention. First mold portion 450 shown in FIG. 4C is configured to receive and support loaded frame 444, and includes recesses 452. In embodiments of method 300, loaded frame 444 may be lowered onto first mold portion 450 in the direction of arrow 438. In embodiments, first mold portion 450 and a second mold portion (not shown) form a pair of mating halves of a mold. The mold is configured such that when the first and second mold portions are brought together, the mold encloses loaded frame 444. As such, once loaded frame 444 is positioned on first mold portion 450, the mold may be closed with conductive elements 434 positioned inside the mold by lowering the second mold portion onto first mold portion 450. In embodiments, the second mold portion includes recesses similar to recesses 452 that, together with recesses 452, form a plurality of cavities when the mold is closed. When loaded frame 444 is positioned on first mold portion 450, conductive elements 434 extend through these cavities formed by the mold.

At block 330 of FIG. 3, the heated, bio-compatible and non-electrically conductive PIM feedstock is injected into the cavities defined by the mold to form insulative bodies 422 around portions of conductive elements 434. In embodiments, the PIM feedstock may be injected around portions of conductive elements 434 such that the resulting insulative bodies 422 completely encapsulate the entire periphery of portions of conductive elements 434. In the embodiment shown in FIGS. 4A-4D, the cavities formed by the mold are configured such that the injected PIM feedstock assumes the shape of insulative bodies 422 shown in FIG. 4D. After injecting the non-electrically conductive PIM feedstock into the mold, the injected PIM feedstock is cooled during a cooling phase so that the feedstock will solidify to form insulative bodies 422. Once insulative bodies 422 have solidified, the mold is opened, and insulative bodies 422 and the conductive elements 434 around which they are formed are removed from the mold. Once removed from the mold, insulative bodies 422 are subjected to a debinding process to remove the binding agents from the solid component.

Figure 4D:
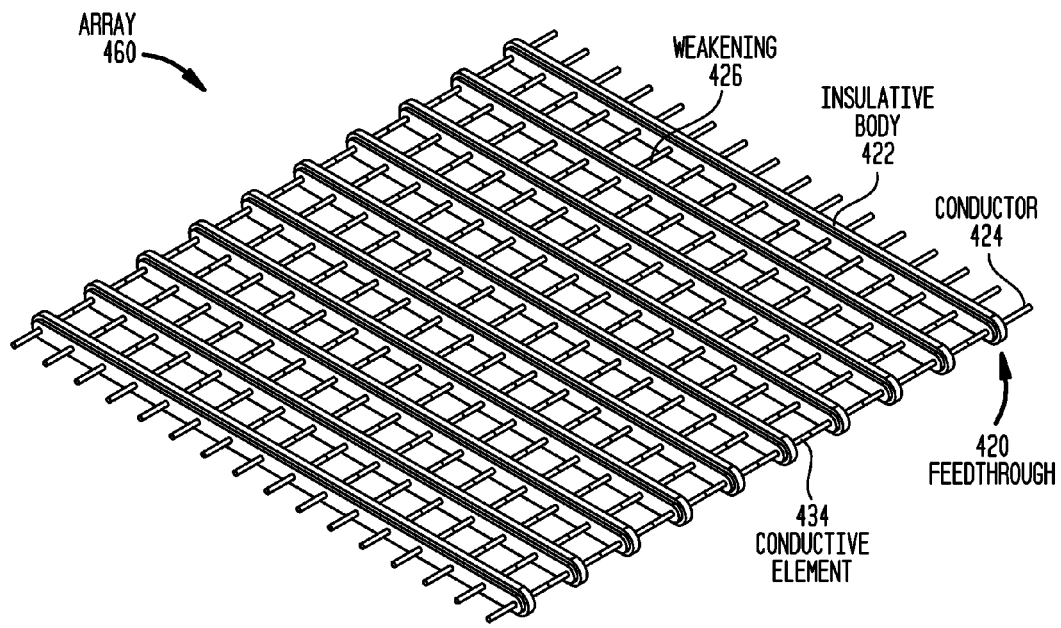
FIG. 4D illustrates an array of feedthroughs formed in accordance with embodiments of the present invention.

FIG. 4D illustrates an array 460 of feedthroughs 420 formed in accordance with embodiments of the present invention. As shown in FIG. 4D, array 460 includes a plurality of physically- and electrically-connected feedthroughs 420. After the debinding process, insulative bodies 422 are sintered, as described above, at block 340 of method 300, to form a plurality of feedthroughs 420. The sintering process causes the particles of each insulative body 422, formed from PIM feedstock, to adhere to one another and also causes insulative body 422 to shrink. In embodiments of the present invention, components formed from injected PIM feedstock may shrink about 10-15% as a result of the sintering process. As shown in FIG. 4D, each feedthrough 420 includes an insulative body 422 and a plurality of conductors 424. In the embodiment illustrated in FIG. 4D, conductive elements 434 pass through each of insulative bodies 422. As such, an array 460 of feedthroughs 420 are physically and electrically connected by conductive elements 434.

After sintering insulative bodies 422, feedthroughs 420 may be physically separated from one another by severing conductive elements 434 between one or more pairs of adjacent insulative bodies 422. In certain embodiments, conductive elements 434 may be severed such that every portion of each conductive element 434 is at least a portion of one of the conductors 424 of one of feedthroughs 420, so that no portion of any conductive element 434 is sacrificed (i.e., discarded). In embodiments of the present invention, insulative bodies 422 are spaced along conductive elements 434 such that, when conductive elements 434 are severed between adjacent insulative bodies 422, each of the resulting conductors 424 has the desired length for its end use in a feedthrough 420. By choosing the amount of space between adjacent insulative bodies 422, the respective lengths of conductors 424 after severing can be controlled so that no portion of any conductive element 434 is sacrificed.

During the sintering process of block 340, feedthroughs 420 are heated to a temperature sufficient to shrink and increase the density of insulative bodies 422 while also substantially removing pores from insulative bodies 422. By substantially removing pores from insulative bodies 422, the sintering process improves the fluid impermeability of insulative bodies 422. An additional advantage of the sintering process is that, as they shrink, insulative bodies 422 constrict more tightly around conductive elements 434, which improves the fluid impermeability of each feedthrough 420 where conductive elements 434 pass through insulative body 422. In addition, the materials used to form insulative bodies 422 and conductive elements 434, and the dimensions of conductive elements 434 may be selected such that, during the high-temperature sintering process, insulative bodies 422 do not enter a liquid phase (i.e., melt) and conductive elements 434 do not expand enough to crack the surrounding insulative bodies 422. Such cracking may occur when conductive elements 434 expand more than can be compensated for by the elasticity of insulative bodies 422. In embodiments of the present invention, the sintering temperature is below the melting temperature of insulative bodies 422 and conductive elements 434. In some embodiments, the sintering temperature may be about 85% of the melting temperature of insulative bodies 422, for example.

In some embodiments, conductors 424 may comprise platinum or niobium. As described above, non-electrically conductive PIM feedstock may include a powdered ceramic, such as aluminum oxide or zirconium oxide. In certain embodiments, it may be preferable to use a conductor comprising platinum and a non-electrically conductive PIM feedstock comprising zirconium oxide because zirconium oxide will securely adhere to platinum better than aluminum oxide will adhere to platinum.

Additionally, in certain embodiments, at least one of conductors 424 may be shaped such that the conductor 424 extends from a first side of an insulative body 422 at a location offset from a location at which the conductor 424 extends from a second side of the insulative body 422. In such embodiments, conductor 424 does not extend straight through the insulative body 422 along a single axis. Alternatively or in addition, at least one of conductors 424 may include an end that is shaped to facilitate connection to one or more functional components. In some embodiments, for example, at least one of conductors 424 may include a shape (e.g. a "bump") in the appropriate part of the conductor to facilitate connection to a functional component. Alternatively or in addition, feedthrough 420 may be integrated into a wall of a housing such that at least one conductor 424 is exposed through a floor of a recess inside the housing. It should be noted that the conductor shapes and locations described above with regard to certain embodiments of the present invention may also be applied to other embodiments of the invention described below. The selected embodiments in which these shapes and locations are described are merely illustrative.

A feedthrough manufactured in accordance with embodiments of the present invention may be integrated into a wall of a container of a housing. For example, a feedthrough 420, manufactured in accordance with embodiments shown in and described with references to FIGS. 3-4D, may be integrated into a wall of a container of a housing, such as housing 102 shown in FIG. 1. Alternatively, in accordance with embodiments of the present invention, a container may be manufactured such that an the insulative body of a feedthrough is unitary with the container.

A conventional implant housing comprises a titanium shell having a biocompatible feedthrough. The use of titanium has certain advantages for relatively large housings due to the relatively high strength and relatively low weight of titanium. However, the formation of relatively small housings using PIM processes in accordance with embodiments of the present invention has several advantages, such as greater design flexibility and lower cost than processes for forming of a housing from titanium. PIM processes in accordance with embodiments of the present invention are also more easily adapted to large-scale production of housings than processes for forming of a housing from titanium. In addition, housings formed using PIM processes in accordance with embodiments of the present invention have adequate strength and weight characteristics.

Figure 5:
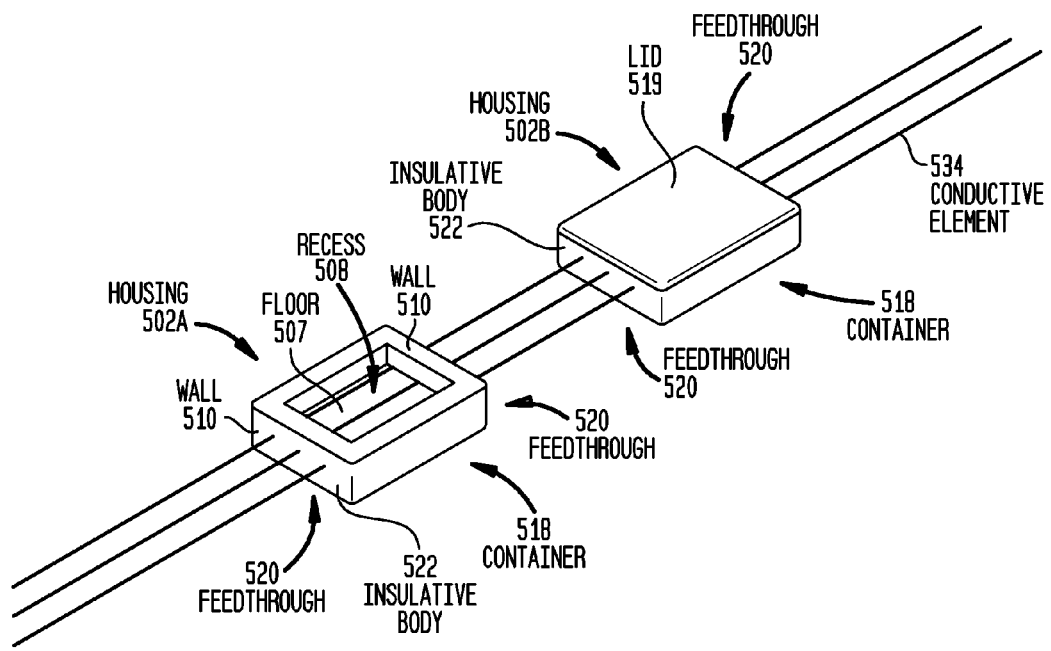
FIG. 5 is a perspective view of a portion of an implantable medical device in accordance with embodiments of the present invention.

FIG. 5 is a perspective view of a portion of an implantable medical device in accordance with embodiments of the present invention. FIG. 5 illustrates two housings 502A and 502B, each of which is formed with feedthroughs 520 in opposing walls of the housing. As shown in FIG. 5, housings 502 are aligned so that continuous conductors, such as conductive elements 534, can extend through each housing 502 to an adjacent housing 502 such that all of housings 502 are physically- and electrically-connected by a plurality of continuous conductive elements 534. In embodiments of the invention, each conductive element 534 may be a unitary conductor that extends through multiple housings 502. In accordance with embodiments of the present invention, any number of housings 502 may be physically- and electrically-connected along conductive elements 534 in FIG. 5. In certain embodiments, one or more of conductive elements 534 extend through and allow electrical communication with each of housings 502. In certain embodiments, some conductive elements may extend through and allow electrical communication with each of the housings 502, while other conductive elements are severed to provide a means of making an electrical connection to an individual housing. As shown, housings 502 are also spaced apart from one another along conductive elements 534. In certain embodiments, housings 502 may be physically separated from one another by severing conductive elements 534 between adjacent housings 502.

In the embodiment shown in FIG. 5, each housing 502 includes a container 518 having a plurality of walls 510 that collectively define a recess 508 and an outer surface of the container 518. Each container 518 also includes a floor 507 in recess 508, a shown in relation to housing 502A. As shown, each container 518 includes multiple feedthroughs 520, each of which includes an insulative body 522 and a plurality of conductive elements 534 that form the conductive paths of the feedthrough. As shown in FIG. 5, the insulative body 522 of each of the feedthroughs 520 is unitary with one of containers 518. In embodiments of the present invention, each insulative body 522 is bio-compatible, electrically insulative and fluid impermeable. Additionally, as shown in the embodiment of FIG. 5, each of a plurality of continuous conductive elements 534 extends from an area external housing 502A, through a first wall 510 of housing 502A into recess 508, along floor 507 of housing 502A, and through a second wall 510 of housing 502A opposite the first wall 510 to another area external housing 502A adjacent the second wall 510. In the embodiment illustrated in FIG. 5, each of conductive elements 534 further extends through another housing 502B adjacent housing 502A as described in relation to housing 502B.

In embodiments of the present invention, feedthroughs 520 may be formed using an embodiment of method 300 illustrated in FIG. 3. In such embodiments, the feedthroughs 520 may be formed in a manner similar to the process for forming feedthroughs 420 described above with regard to FIGS. 3-4D, except that the mold defines cavities having the shape of containers 518 rather than the shape of insulative bodies 422. As such, containers 518 with unitary insulative bodies 522 my be formed by injecting non-electrically conductive PIM feedstock into the mold, as described above. Additionally, in some embodiments, a plurality of containers 518 may be simultaneously formed around one or more continuous conductors, such as conductive elements 534.

In alternative embodiments of the present invention, feedthroughs 520 having insulative bodies 522 unitary with containers 518, as shown in FIG. 5, may also be formed in accordance with the method described below in relation to FIGS. 6-7H. Forming insulative bodies 522 that are unitary with containers 518, in accordance with some embodiments of the present invention, eliminates an interface created between a housing wall and an insulative body when a feedthrough is integrated into the housing wall. This interface may be susceptible to fluid leakage, so embodiments of the present invention may eliminate the potential for fluid leakage at the interface.

After forming containers 518 as described above, a lid 519 may be hermetically sealed to each container 518 to form a bio-compatible and hermetically-sealed housing 502. In the embodiment shown in FIG. 5, housing 502B includes a lid 519 that is hermetically sealed to container 518. While not shown, housing 502A may also include a lid 519 hermetically sealed to container 518. In some embodiments, lids 519 are formed by the same PIM process used to form containers 518. For example, lids 519 may be formed in the same mold used to form containers 518, but in different mold cavities.

In the embodiment illustrated in FIG. 5, containers 518 are molded around conductive elements 534 such that conductive elements 534 are exposed inside recess 508. As such, each conductive element 534 provides a conductive path from the exterior to the interior of a container 518 and providing a common conductive path to all housings 502. In such embodiments, the one or more functional components are mounted in recess 508 and electrically connected to one or more of conductive elements 534 exposed within recess 508. Such functional components may be, for example, analog/digital circuits, processors, application-specific integrated circuits (ASICs) or other integrated circuits (ICs). In some embodiments, an IC may be mounted and electrically connected to one or more of the conductive elements 534 using a flip-chip bonding process. In addition or alternatively, one or more functional components may be mounted in recess 508 and then electrically connected to one or more of conductive structures 534 using wires or other conductors.

In some embodiments of the present invention, two or more of housings 502 are not physically separated from one another. The housings 502 that remain physically connected by conductive elements 534 thereby form a chain of housings 502 that are physically- and electrically-connected by conductive elements 534. In embodiments in which the chain of housings 502 is used as a component of an implantable device, the conductive elements 534 may be covered with a biocompatible, electrically insulative material before the device is implanted.

In some embodiments, each conductive element 534 is exposed within the recess 508 of each container 518, such that each of conductive elements 534 is available for electrical connection to any functional component that is, or will be, mounted in a container 518. In other embodiments, one or more of conductive elements 534 physically connecting a plurality of housings 502 are not accessible for electrical connection within the recesses 508 of some housings 502. In such embodiments, certain containers 518 may be shaped to encapsulate certain conductive elements 534 that would otherwise be exposed within recess 508. Additionally or alternatively, one or more containers 518 may be offset, relative to other containers 518, so that one or more conductive elements 534 are encapsulated by walls 510 throughout the housing and not exposed in recess 508. In addition or alternatively, certain conductive elements 534 may include various bends such that conductive elements 534 are exposed in the recesses 508 of some containers 518 are not exposed within the recesses 508 of the other containers 518.

In certain embodiments of the present invention, containers 518 are spaced along conductive elements 534 such that, when conductive elements 534 are severed between adjacent containers 518, each of the resulting conductors severed from a conductive elements 534 has the desired length for its end use in a housing 502. By choosing the amount of space between adjacent containers 518, the respective lengths of conductors severed from conductive elements 534 can be controlled so that no portion of any conductive element 534 is sacrificed. Additionally, using PIM processes in accordance with embodiments of the invention allows insulative bodies to be formed in a wide variety of shapes.

FIG. 6 is a flowchart illustrating a method 600 of forming a feedthrough 720 using PIM in accordance with embodiments of the present invention. FIGS. 7A-7H illustrate elements used in or resulting from various aspects of FIG. 6. For ease of explanation, the embodiments of FIG. 3 will be described with reference to the elements illustrated in FIGS. 7A-7H.

Figure 7A:
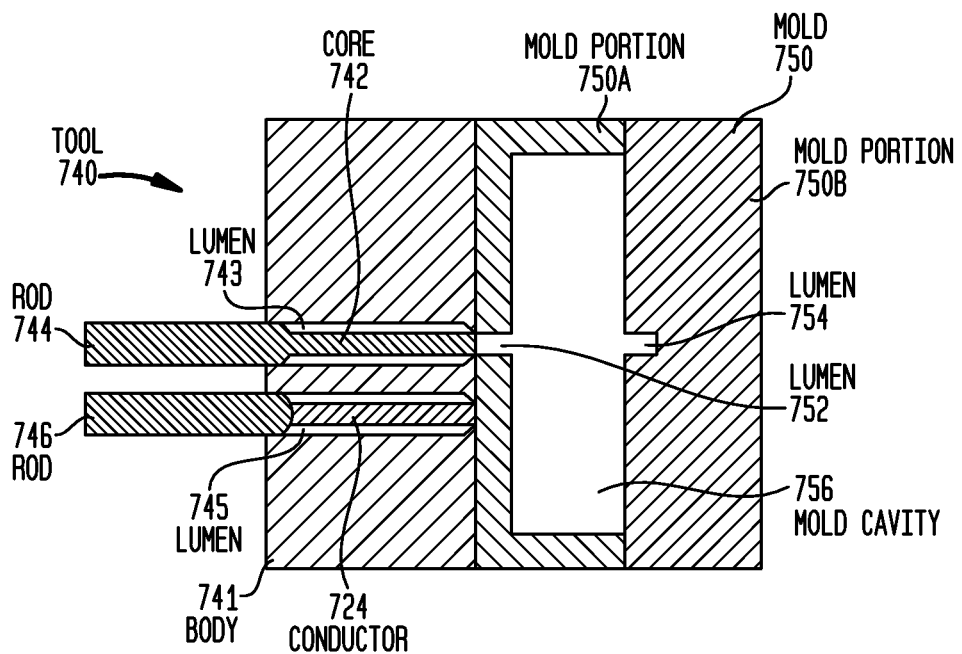
FIGS. 7A-7H are cross-sectional views of a mold and a tool that may be used to form a feedthrough in accordance with embodiments of the present invention.
Figure 7B:
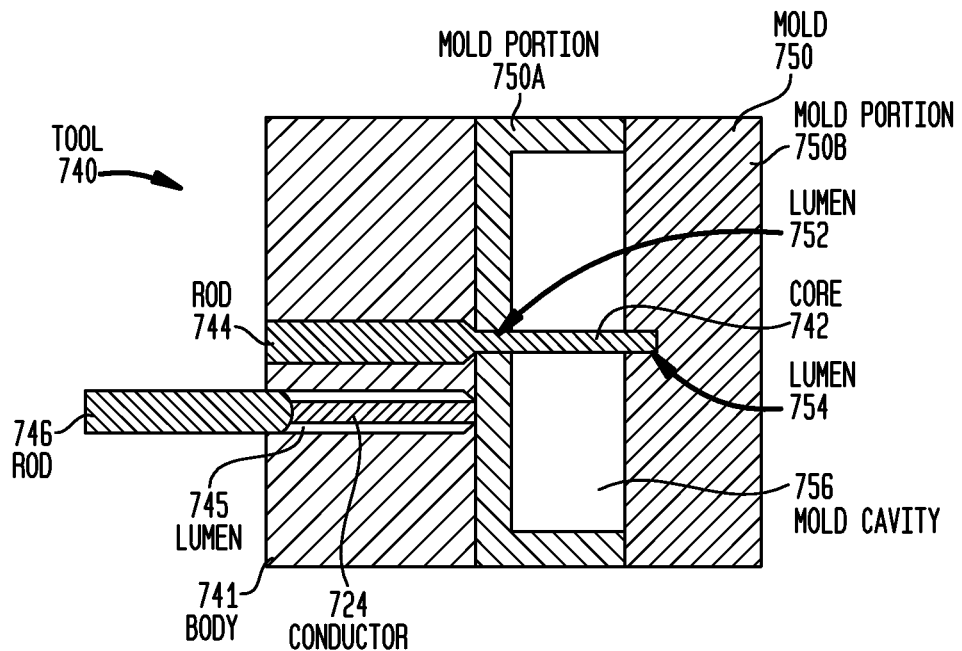
Figure 7C:
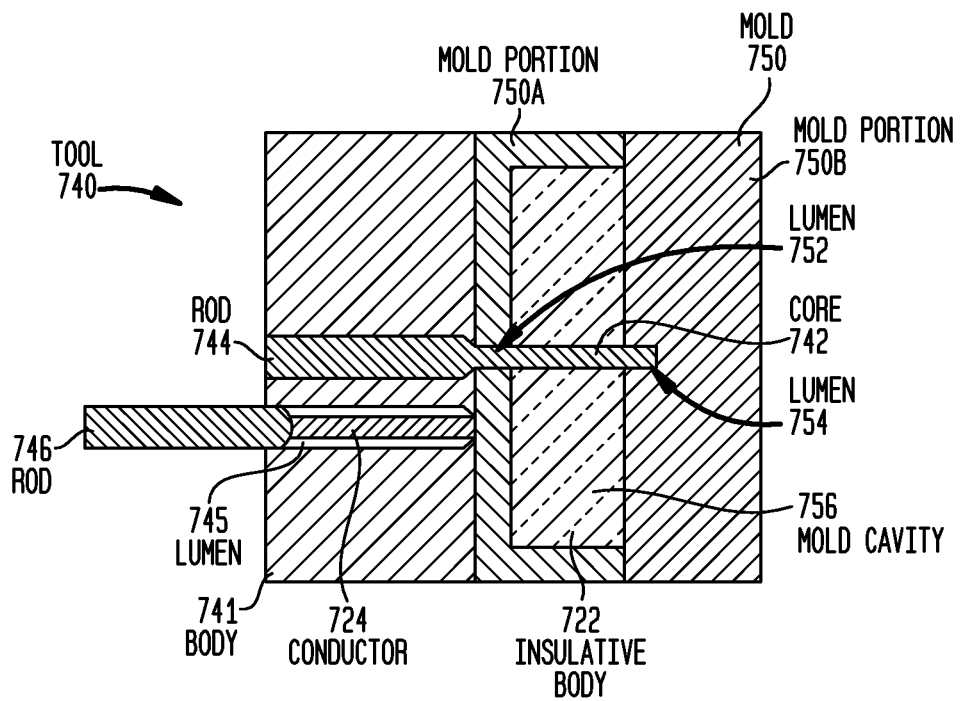
Figure 7D:
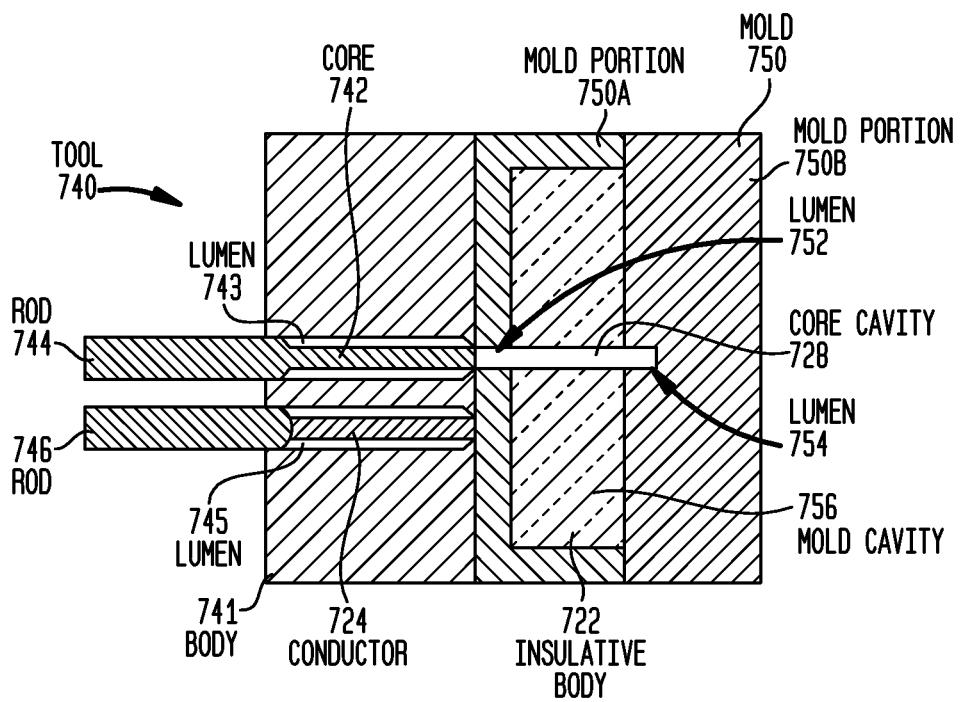
Figure 7E:
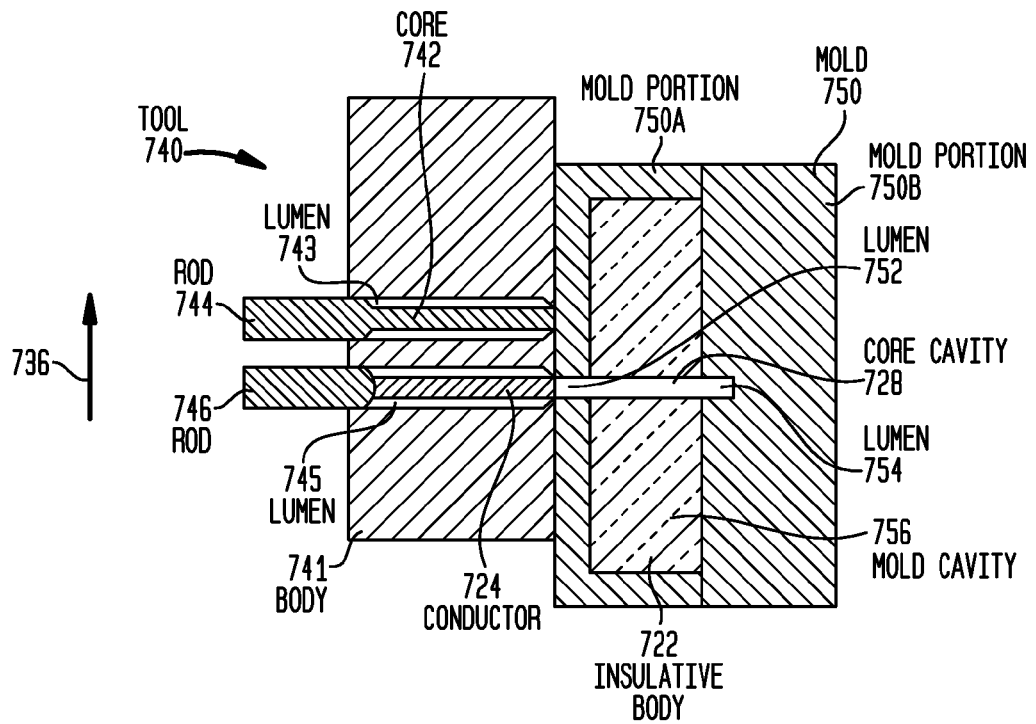
Figure 7F:
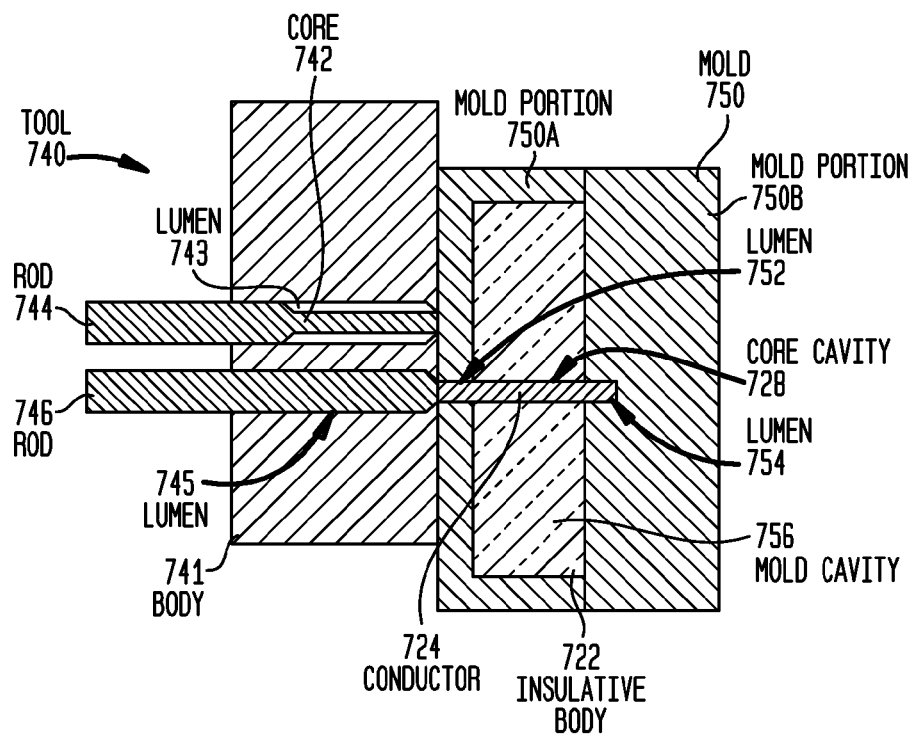
Figure 7G:
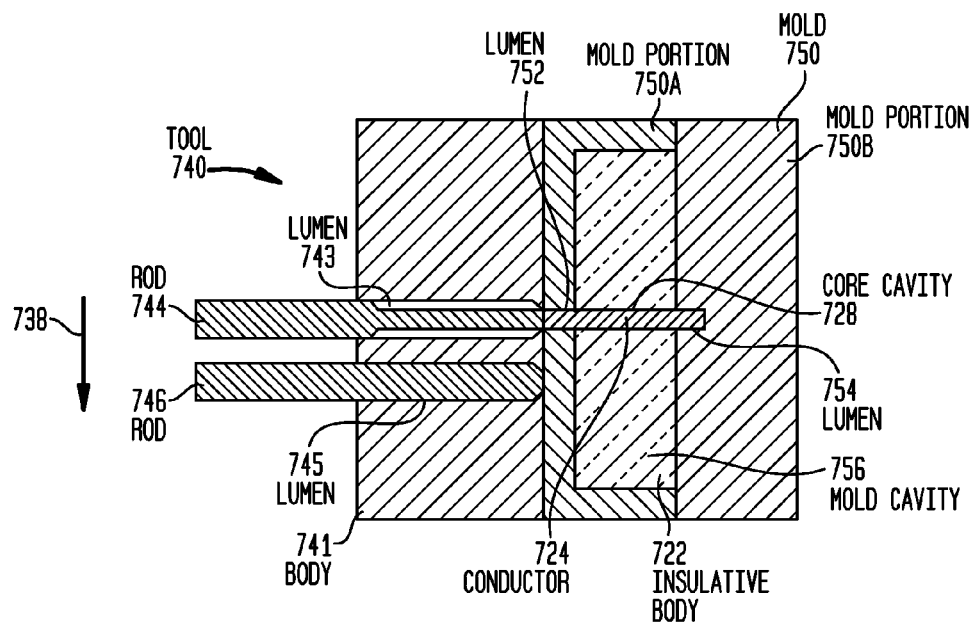
Figure 7H:
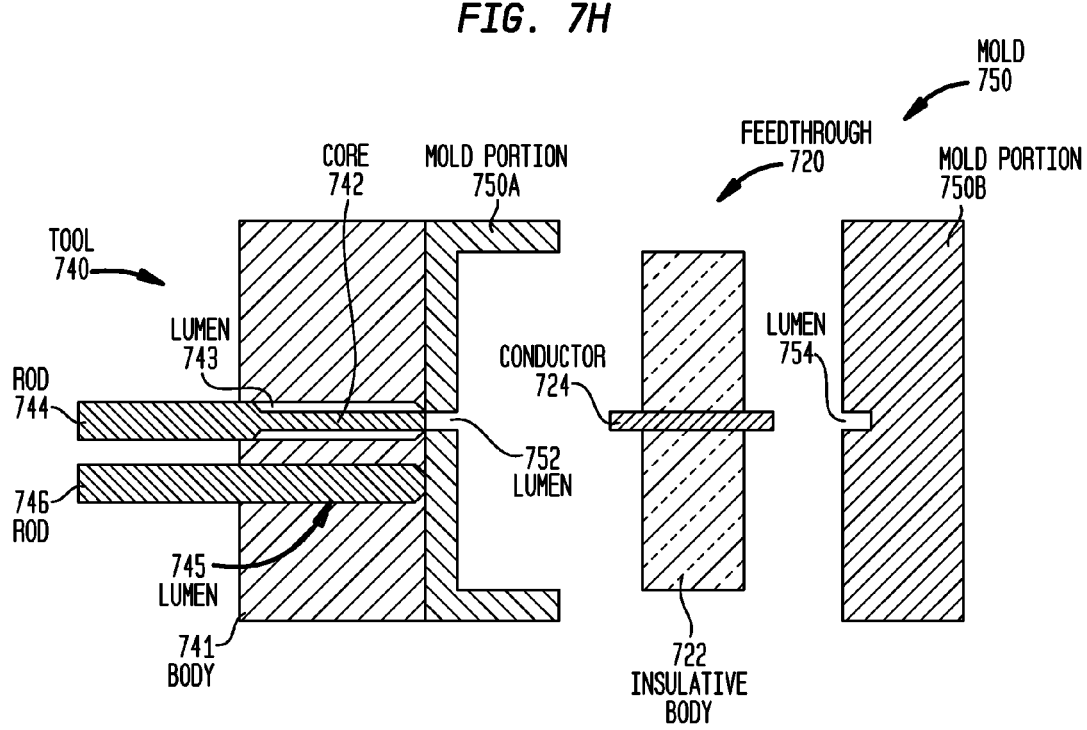

FIGS. 7A-7H are cross-sectional views of a mold 750 and a tool 740 that may be used to form a feedthrough 720 in accordance with embodiments of the present invention. Feedthrough 720 shown in FIG. 7H is an embodiment of feedthrough 120 of FIG. 1, and may be integrated into a hermetically sealed housing, as illustrated in FIG. 1, for example. As shown in FIG. 7A, mold 750 includes first and second mold portions 750A and 750B that define a mold cavity 756 when closed. Mold portion 750A includes one or more lumens 752 and mold portion 750B includes one or more lumens 754 that are aligned with lumens 752, respectively, when mold 750 is closed. Tool 740 includes a body 741 having two lumens 743 and 745, and a rod 744 that moves a core 742 connected to rod 744 through lumen 743. Tool 740 further includes a rod 746 configured to move a conductor 724 out of lumen 745, as described below.

Method 600 illustrated in FIG. 6 begins at block 610 at which a bio-compatible and non-electrically conductive PIM feedstock is heated to facilitate injection into mold 750. At block 620, core 742 is moved into mold cavity 756, as shown in FIG. 7B. As illustrated in FIG. 7A, mold 750 is closed and body 741 of tool 740 is positioned such that lumen 743 is aligned with lumens 752 and 754. Rod 744 then moves core 742 into mold cavity 756 by pushing core 742 out of lumen 743 such that one end of core 742 passes through lumen 752 and mold cavity 756, and moves into lumen 754. FIG. 7B shows core 742 after it has been moved into mold cavity 756. While the embodiment illustrated in FIG. 6 begins with heating the PIM feedstock, in alternative embodiments, core 742 may be moved into mold cavity 756 before the PIM feedstock is heated or while the feedstock is being heated.

At block 630, the heated PIM feedstock is then injected into mold cavity 756, at block 630, in order to form an insulative body 722 around core 742, as shown in FIG. 7C. At block 640, core 742 is removed from mold 750 and insulative body 722 by rod 744, as shown in FIG. 7D, during a cooling phase in which the injected PIM feedstock is cooled from the elevated temperature at which it was injected. As illustrated in FIG. 7D, removing core 742 from insulative body 722 leaves a cavity in insulative body 722, referred to herein as core cavity 728. Body 741 is then moved in the direction indicated by arrow 736 to align lumen 745 with core cavity 728 and lumens 752 and 754, as shown in FIG. 7E.

At block 650, conductor 724 is inserted into core cavity 728 during a cooling phase of the PIM process during which insulative body 722 cools from the elevated temperature at which the PIM feedstock was injected. As shown in FIGS. 7E and 7F, conductor 724 is moved out of lumen 745 and into core cavity 728 by rod 746 such that conductor 724 is disposed partially in core cavity 728 and partially in each of lumens 752 and 754. In embodiments, conductor 724 may be inserted into core cavity 728 such that insulative body 722 completely encapsulates the entire periphery of at least a portion of conductor 724. In embodiments of the present invention, the diameter of core cavity 728 may be smaller than the diameter of conductor 724. In such embodiments, conductor 724 is pressed into core cavity 728 and forms an interference fit with insulative body 722. In other embodiments, the diameter of core cavity 728 may be greater than or equal to the diameter of conductor 724.

By inserting conductor 724 into insulative body 722 during the cooling phase (i.e., while insulative body 722 is still relatively hot), conductor 724 will be in place in core cavity 728 while insulative body 722 cools. As such, once conductor 724 is in place in insulative body 722, insulative body 722 will constrict around conductor 724 as it continues to cools. Allowing insulative body 722 to constrict around conductor 724 as it cools helps ensure that conductor 724 will remain in place in insulative body 722 during subsequent debinding and sintering processes without the need for fixtures designed to hold conductor 724 in place during these processes. Additionally, it is noted that inserting conductor 724 into insulative body 722 as described above does not increase manufacturing time because conductor 724 is inserted into insulative body 722 during the typical cooling period for a PIM process.

As shown in FIG. 7G, body 741 of tool 740 may be moved in the direction of arrow 738 to return body 741 to its starting position in which lumen 743 is aligned with lumen 752. As illustrated in FIG. 7H, mold 750 may be opened and insulative body 722 with conductor 724 disposed in insulative body cavity 728 may be removed or ejected from mold 750. Once removed from the mold, insulative body 722 is subjected to the debinding process described above. After the debinding process, insulative body 722 is sintered, as described above, at block 660 to form feedthrough 720.

For clarity of description, embodiments illustrated in FIGS. 6-7H were shown and described with reference to the insertion of one exemplary conductor 724 into insulative body 722. However, in embodiments of the present invention, tool 740 may comprise any number of cores 742 and conductors 724 for insertion into mold cavity 756, and mold 750 may comprise any number of lumens 752 and 754 for receiving cores 742 and conductors 724. In such embodiments, mold 750 and tool 740 are configured to form an insulative body 722 having a plurality of conductors 724 disposed in insulative body 722, and tool 740 may be configured to insert the plurality of conductors 724 into insulative body 722 simultaneously or in any other order. In addition, the embodiments of method 600 shown and described in relation to FIGS. 6-7H are preferably performed by an automated system, but may also be performed manually. Embodiments of the method shown and described above with reference to FIGS. 6-7H may also be used to form feedthroughs having insulative bodies unitary with containers, as shown and described above with reference to FIG. 5. In such embodiments, mold 750 may be configured to form containers 518 when the PIM feedstock is injected into the mold, and conductive elements 534 may be inserted through core cavities formed in containers 518 during the cooling phase. After performing debinding and sintering processes, the lids 519 may be hermetically sealed to containers 518 to form a plurality of physically- and electrically-connected housings 502 as illustrated in FIG. 5.

Figure 8:
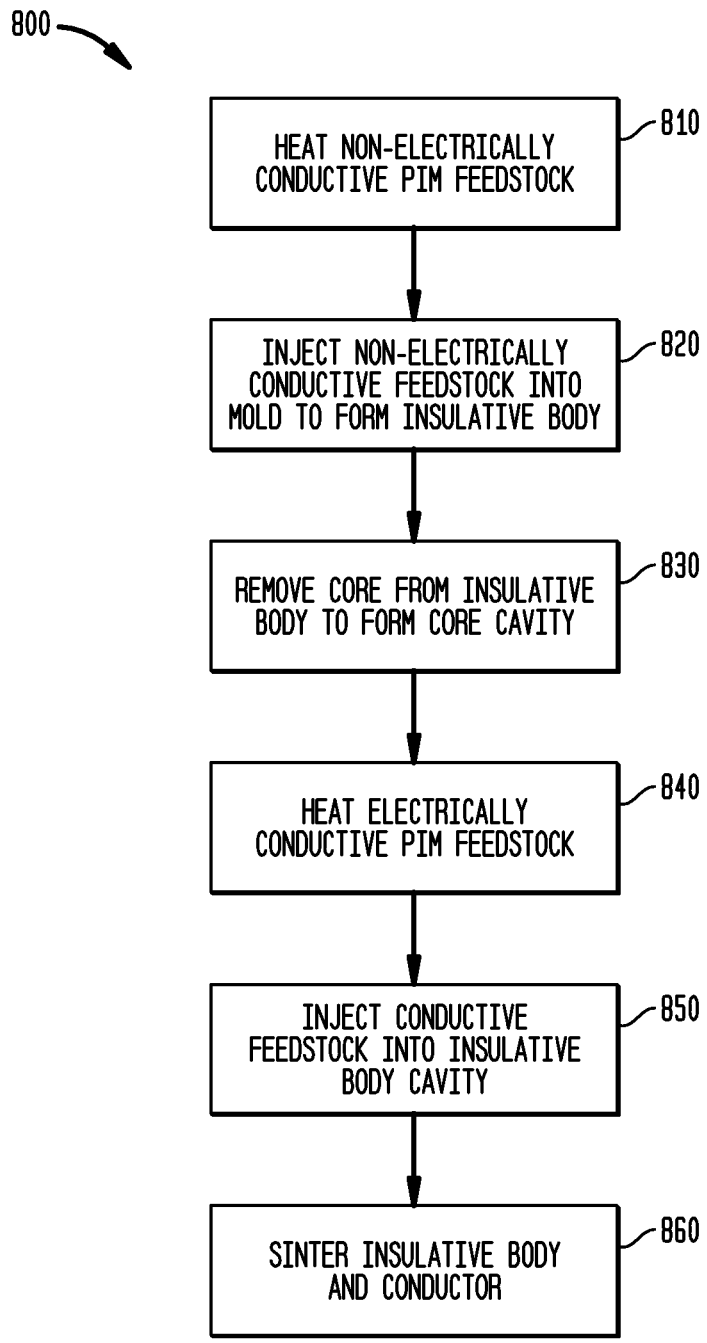
FIG. 8 is a flowchart illustrating a method of forming a feedthrough using two-material PIM in accordance with embodiments of the present invention.

FIG. 8 is a flowchart illustrating a method 800 of forming a feedthrough using two-material PIM in accordance with embodiments of the present invention. As used herein, "two-material PIM" refers to a type of two-color or two-component injection molding in which one type of PIM feedstock is used to form one or more parts of a structure and another type of PIM feedstock is used to form one or more other parts of the structure. In accordance embodiments of the present invention, for example, an non-electrically conductive PIM feedstock may be used to form the insulative body of a feedthrough and an electrically conductive PIM feedstock may be used to form the conductive paths of the feedthrough. FIGS. 9A-9E illustrate elements used in or resulting from various aspects of FIG. 8. For ease of explanation, the embodiments of FIG. 8 will be described with reference to the elements illustrated in FIGS. 9A-9E.

Figure 9A:
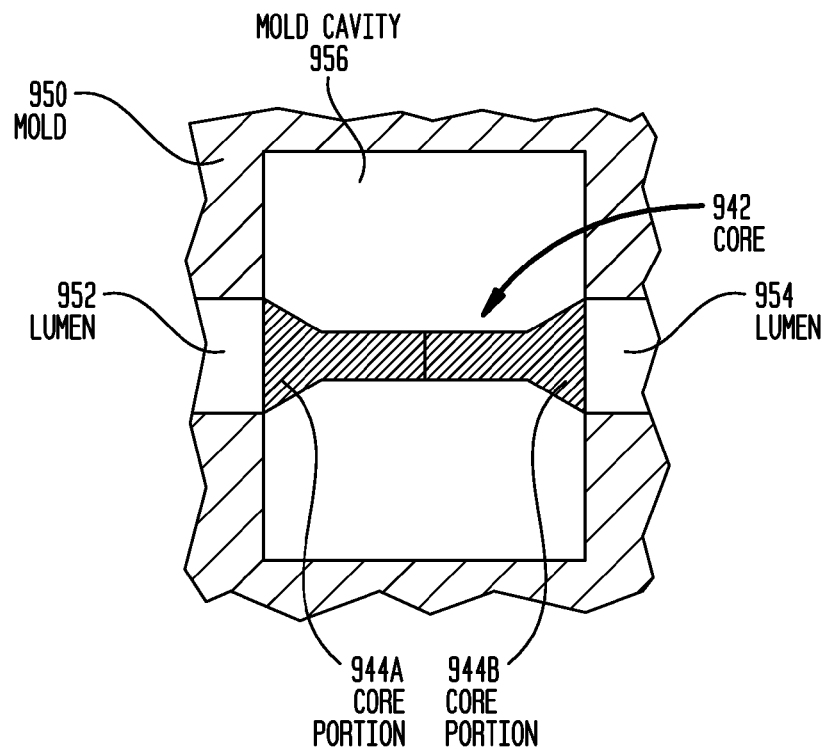

FIGS. 9A-9E are cross-sectional views illustrating the formation of a feedthrough 920 using a mold 950 in accordance with embodiments of the method illustrated in FIG. 8. As shown in FIG. 9A, mold 950 defines a mold cavity 956 when mold 950 is closed, and includes lumens 952 and 954. The shape of mold cavity 956 shown in FIG. 9A is just one exemplary shape of mold cavity 956, in accordance with an embodiment of the present invention. In embodiments of the present invention, mold cavity 956 may have any shape desired. In some embodiments, for example, mold cavity 956 may be shaped to form an insulative body similar to insulative body 422 shown in FIG. 4A when PIM feedstock is injected into the mold cavity. In alternative embodiments, mold cavity 956 may be shaped to form a container or one or more walls of a container when PIM feedstock is injected into the mold cavity. Additionally, in the embodiment shown in FIG. 9A, a core 942, which includes first and second core portions 944A and 944B, is disposed in mold cavity 956. In other embodiments, core 942 may have any shape desired. For example, in certain embodiments, core 942 may be a unitary core shaped such that it may be readily withdrawn from mold cavity 956 after injecting PIM feedstock. In other embodiments, core 942 may comprise any number of separate pieces.

Figure 9B:
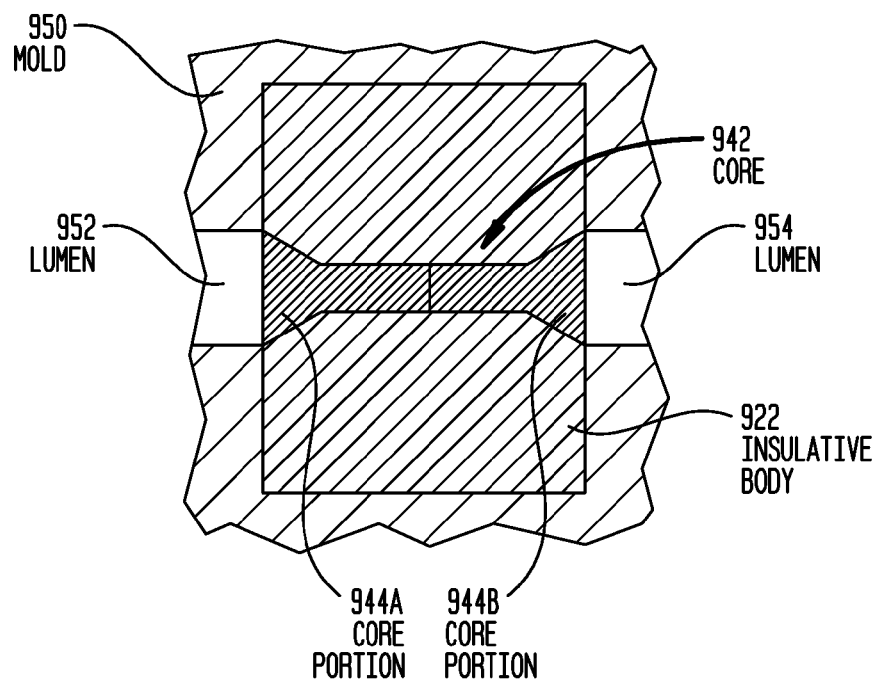

Method 800 illustrated in FIG. 8 begins at block 810 at which a bio-compatible and non-electrically conductive PIM feedstock is heated to facilitate injection into mold 950. At block 820, the heated, non-electrically conductive PIM feedstock is injected into mold cavity 956 in order to form an insulative body 922 around core 942, as shown in FIG. 9B. At block 830, core 942 is removed from insulative body 922. In the embodiment illustrated in FIGS. 9A-9E, core 942 is removed from insulative body 922 by moving core portions 944A and 944B away from one another out of mold cavity 956. As shown in FIG. 9C, core portions 944A and 944B are moved out of insulative body 922 and into lumens 952 and 954, respectively. Moving core 942 out of insulative body 922 leaves a cavity in insulative body 922, referred to herein as a core cavity 928. An electrically conductive PIM feedstock is heated at block 840. As described above, the electrically conductive PIM feedstock is heated to facilitate injection into mold 950.

As shown in FIG. 9D, the heated, electrically conductive PIM feedstock is injected into core cavity 928 to form a conductor 924 in insulative body 922 at block 850. By injecting the electrically conductive PIM feedstock into core cavity 928, conductor 924 assumes the shape of core cavity 928. As such, in embodiments of the present invention, conductors of many different shapes may be formed by using a single- or multi-part core 942 having the desired shape. As shown in FIGS. 9A-9E, conductor 924 includes a central portion 929 between two ends 925 and 927, where the diameter of central portion 929 is smaller than the respective diameters of ends 925 and 927. In addition, each of ends 925 and 927 has a diameter greater than the diameter of a central portion of core cavity 928. As such, once formed in core cavity 928, conductor 924 illustrated in FIG. 9E is prevented from moving out of insulative body 922 easily. In addition, in the embodiment shown in FIG. 9E, the shape of conductor 924 matches the shape of core cavity 928, so insulative body 922 will substantially prevent any movement of conductor 924 relative to insulative body 922. In embodiments, conductor 924 may be formed in core cavity 928 such that insulative body 922 completely encapsulates the entire periphery of at least a portion of conductor 924.

Insulative body 922 and conductor 924 may then be removed from mold 950, as shown in FIG. 9E. Once removed from mold 950, insulative body 922 and conductor 924 are subjected to a debinding process. At block 860, insulative body 922 and conductor 924 are sintered, as described above, to form feedthrough 920. In addition, forming both the insulative body and the conductor from PIM feedstock in accordance with embodiments of the invention has the additional advantage that particles in each of those components adhere to one another as a result of the sintering process, which may provide a better hermetic seal than when an insulative body is shrunk to constrict around a conductor that is not formed from PIM feedstock. In certain embodiments, the powder components of the respective PIM feedstocks used to form the insulative body and the conductor will adhere to one another. As one example, when the electrically conductive and non-electrically conductive PIM feedstocks used both include an aluminum oxide powder component, the aluminum oxide parts of the insulative body and the aluminum oxide parts of the conductor will be continuous after sintering. This physical continuity resulting from the use of PIM feedstock to form both the insulative body and the conductor provides a better hermetic seal between the insulative body and the conductor than feedthroughs in which only one of the insulative body and the conductor is formed from a PIM feedstock. Additionally, using two-material PIM to form a feedthrough in accordance with embodiments of the invention allows both the insulative body and the conductor(s) of a feedthrough to be formed in a large variety of shapes, as described above in reference to the embodiments of FIGS. 9A-9E. In addition to providing wide design flexibility, two-material PIM is also a highly scalable manufacturing process.

While the embodiment illustrated in FIG. 8 shows heating the electrically conductive PIM feedstock after removing core 942 at block 830, in alternative embodiments, the electrically conductive PIM feedstock may be heated at any time prior to the injection of the electrically conductive PIM feedstock into insulative body cavity 928. For example, in embodiments, the electrically conductive PIM feedstock may be heated before, during or after any of heating the non-electrically conductive PIM feedstock at block 810, injecting the non-electrically conductive PIM feedstock at block 820, and removing core 942 at block 830.

For clarity of description, embodiments illustrated in FIGS. 8-9E were shown and described with reference to the formation of one exemplary conductor 924 in an insulative body 922. However, in embodiments of the present invention, mold 950 comprise any number of cores 942 and corresponding lumens, and also may be configured to form any number of conductors 924 in an insulative body 922. In certain embodiments, for example, mold 950 and is configured to form an insulative body 922 having a plurality of conductors 924 disposed in insulative body 922. Additionally, embodiments of the method shown and described above in relation to FIGS. 8-9E may be used to form a feedthrough that is integrated into a wall of a housing. Alternatively, embodiments of the method may be used to form a feedthrough in which the insulative body is unitary with the wall of a housing. In such embodiments, the mold cavity 956 may be configured to form a container similar to the container 518 illustrated in FIG. 5, and conductors 924 may be formed in walls of the container. The embodiments of method 800 shown and described in relation to FIGS. 8-9E are preferably performed by an automated system.

When forming a structure using a two-material PIM process, it is preferable to select the two PIM feedstocks such that elements formed from one of the feedstocks will not crack or otherwise damage elements formed from the other feedstock when the structure is sintered. For a discussion of these issues see, for example, Johnson et al., "Design Guidelines for Processing Bi-Material Components via Powder-Injection Molding," Journal of the Minerals, Metals and Materials Society, vol. 55, no. 10, pgs. 30-34 (October 2003). It is preferred that, when an element is sintered, a first portion formed from one of the feedstocks does not exert a force on a second portion that is greater than the second portion's elastic limit. That is, the materials of the two PIM feedstocks are preferably be chosen so as to closely match the sintering dynamics of the feedstocks.

In accordance with embodiments of the present invention, two-material PIM processes used to form feedthroughs, as described herein, may utilize electrically conductive and non-electrically conductive PIM feedstocks that each include a powdered ceramic. The use of two PIM feedstocks that both include powdered ceramic in embodiments of the invention is advantageous because the sintering dynamics of the two feedstocks are very similar. In alternative embodiments, the non-electrically conductive PIM feedstock may include ceramic powder, while the electrically conductive PIM feedstock may include niobium powder. In such embodiments, this combination of feedstocks may be advantageous because the respective coefficients of thermal expansion for these two materials are within 10% of one another. Additionally, an advantage of forming conductive paths using a PIM feedstock including niobium rather than using a pre-formed platinum conductor, in embodiments of the invention, is that niobium is biocompatible metal that is less expensive than platinum.

FIGS. 10A and 10B schematically illustrate an injection molding apparatus 1000 that may be used to perform two-material PIM in accordance with embodiments of the present invention. In certain embodiments of the present invention, molding apparatus 1000 may be used to perform the process illustrated in FIGS. 9A-9E. As shown in FIG. 10A, molding apparatus 1000 includes a first hopper 1070 that feeds a first feedstock into a first injection apparatus 1072 and a second hopper 1074 that feeds a second feedstock into a second injection apparatus 1076. In embodiments, first hopper 1070 may include non-electrically conductive PIM feedstock and second hopper 1074 may include electrically conductive PIM feedstock. First and second injection apparatuses 1072 and 1076 are aligned with gate apertures 1075 and 1077 of a gate 1078. Molding apparatus 1000 further includes a mold 1050 that is movable relative to gate 1078.

When performing a two-material PIM process in accordance with embodiments of the present invention, a mold aperture 1055 of mold 1050 may be aligned with gate aperture 1075 of gate 1078, as shown in FIG. 10A. In embodiments, injection apparatus 1072 receives the non-electrically conductive PIM feedstock from hopper 1070 and then heats the received feedstock. With a core 1042 disposed in a mold cavity 1056 of mold 1050, injection apparatus 1072 injects the heated feedstock into through gate aperture 1075 and mold aperture 1055 into a mold cavity 1056 to form an insulative body 1022 (illustrated in FIG. 10B) around core 1042 in mold cavity 1056.

Mold 1050 may then move relative to gate 1078 to align mold aperture 1057 with gate aperture 1077, as shown in FIG. 10B. In embodiments, injection apparatus 1076 receives the electrically conductive PIM feedstock from hopper 1074 and then heats the received feedstock. As shown in FIG. 10B, core portions 1044A and 1044B may be moved out of mold cavity 1056 and into lumens 1052 and 1054, respectively, to form a core cavity 1028 in insulative body 1022. Injection apparatus 1076 may then inject the heated, electrically conductive feedstock into core cavity 1028 to form a conductor in core cavity 1028 (see, for example, FIG. 9D). In embodiments, the conductor may be formed in core cavity 1028 such that insulative body 1022 completely encapsulates the entire periphery of at least a portion of the conductor. Mold 1050 may then be opened and insulative body 1022 and the conductor may be removed and subjected to debinding and sintering processes, as described above in relation to the embodiment illustrated in FIGS. 9A-9E. In embodiments of the invention, various different molds 1050 may be used to form insulative bodies of various different shapes. For example, in certain embodiments mold cavity 1056 may be configured to form an insulative body that may be integrated into a wall of a housing, while in other embodiments, mold cavity 1056 may be configured to form a container including at least one feedthrough having an insulative body that is unitary with at least one wall of the container.

Figure 11A:
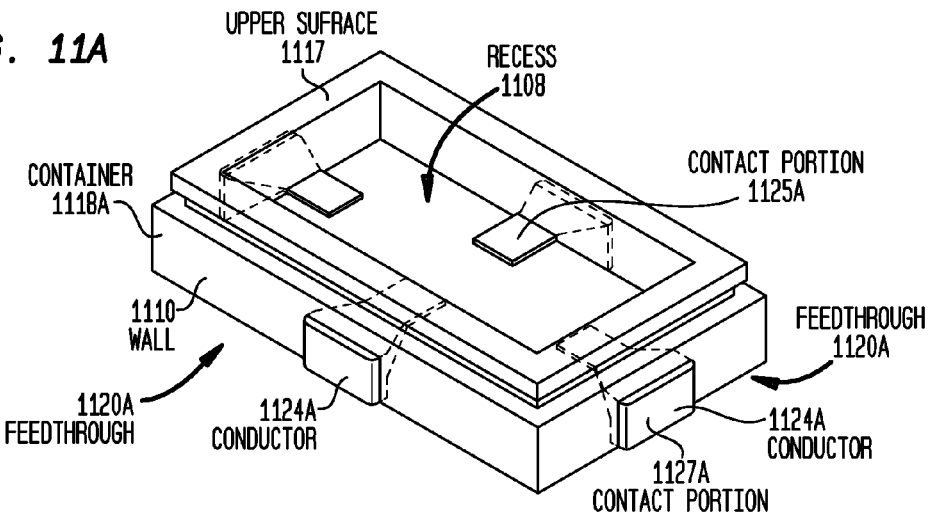
FIG. 11A is a perspective view of feedthroughs of a container, where the feedthroughs may be formed in accordance with embodiments of the present invention.

FIG. 11A is a perspective view of feedthroughs 1120 of a container 1118, where the feedthroughs may be formed in accordance with embodiments of the present invention. In the embodiment illustrated in FIG. 11A, container 1118 is non-electrically conductive and includes a plurality of walls 1110 that form sidewalls and a bottom of container 1118, and which define a recess 1108. As shown, a plurality of conductors 1124 extend through respective walls 1110 of container 1118 to form feedthroughs 1120, each of which includes an insulative body unitary with a wall 1110 and a conductor 1124 forming a conductive path through the wall. In embodiments, each conductor 1124 is exposed both within recess 1108 and at an outer surface of container 1118.

Feedthroughs 1120 may be formed in accordance with embodiments of method 800 illustrated above in FIG. 8. In certain embodiments, feedthroughs 1120 may be formed in accordance with the process described above with reference to FIGS. 9A-9E. In such embodiments, mold cavity 956 is shaped to form container 1118 when the non-electrically conductive PIM feedstock is injected into mold cavity 956. Single- or multi-piece cores 942 having the shape of conductors 1124 are disposed in mold cavity 956 when the non-electrically conductive PIM feedstock is injected in order to form core cavities 928 in container 1118. After removing cores 942, electrically conductive PIM feedstock is injected into the core cavities to form conductors 1124 that extend through walls 1110 of container 1118. Container 1118 and conductors 1124 may then be removed from the mold and subjected to debinding process and a sintering process as described above, to form feedthroughs 1120. Each feedthrough 1120 includes an insulative body unitary with container 1118, and at least one conductor 1124 forming a conductive path through the insulative body. As shown in FIG. 11A, a planar first contact portion 1125A of each of conductors 1124A is exposed within recess 1108. In embodiments, each of first contact portions 1125A is disposed on the same surface within recess 1108. In embodiments, each of conductors 1124A also includes a planar second contact portion 1127A that is parallel with the wall 1110 in which it is exposed and perpendicular to planar first contact portion 1125A of the same conductor 1124A.

In certain embodiments, after forming feedthroughs 1120 in container 1118, one or more functional components may be mounted in recess 1108, and a lid may be hermetically sealed on container 1118 at upper surface 1117 and over recess 1108 to form a hermetically sealed housing. In embodiments, the one or more functional components are mounted in recess 1108 and electrically connected to one or more of conductors 1124A via first contact portions 1125A. In certain embodiments, one or more of the functional components may be an integrated circuit (IC) that is mounted and electrically connected to one or more of first contact portions 1125A using a flip-chip bonding process. In addition or alternatively, one or more functional components are mounted in recess 1108 and then electrically connected to one or more of first contact portions 1125A using wires or other conductors. In some embodiments, the lid hermetically sealed on container 1118 may be similar to lid 519 shown in FIG. 5

Figure 11B:
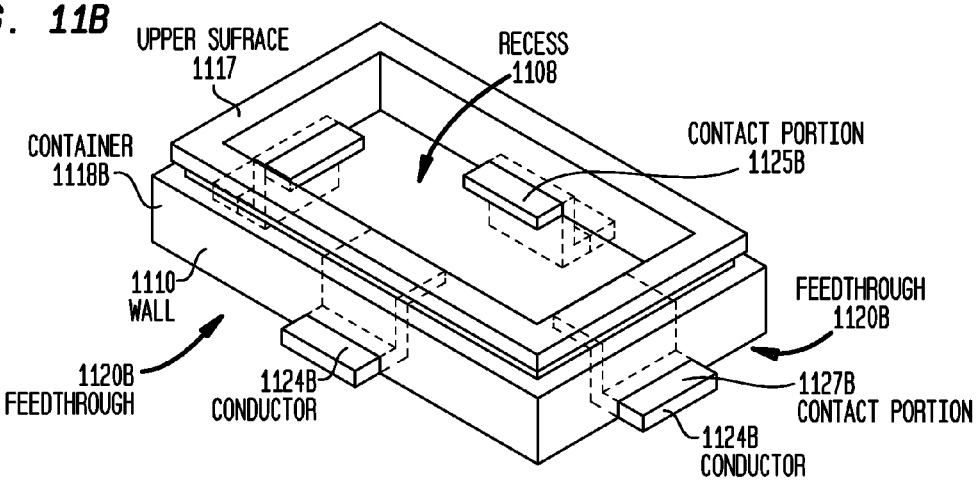
FIG. 11B is a perspective view of feedthroughs of another container, where the feedthroughs may be formed in accordance with other embodiments of the present invention.

FIG. 11B is a perspective view of feedthroughs 1120B of another container 1118B, where the feedthroughs may be formed in accordance with other embodiments of the present invention. Container 1118B and feedthroughs 1120B are similar to container 1118A and feedthroughs 1120A, except that conductors 1124B of feedthroughs 1120B have a different shape than conductors 1124A of feedthroughs 1120A. As shown in FIG. 11B, each of conductors 1124B is shaped like a step, having a first contact portion 1125B exposed on an inner surface of recess 1108 and a second contact portion 1127B exposed at and extending from a wall 1110 adjacent a bottom surface of container 1118B opposite upper surface 1117. Container 1118B with feedthroughs 1120B may be formed by a process similar to the process described above with reference to FIG. 11A, except that, instead of cores 942, the process may utilize single- or multi-piece cores used to form core cavities 928 shaped like conductors 1124B.

Figure 11C:
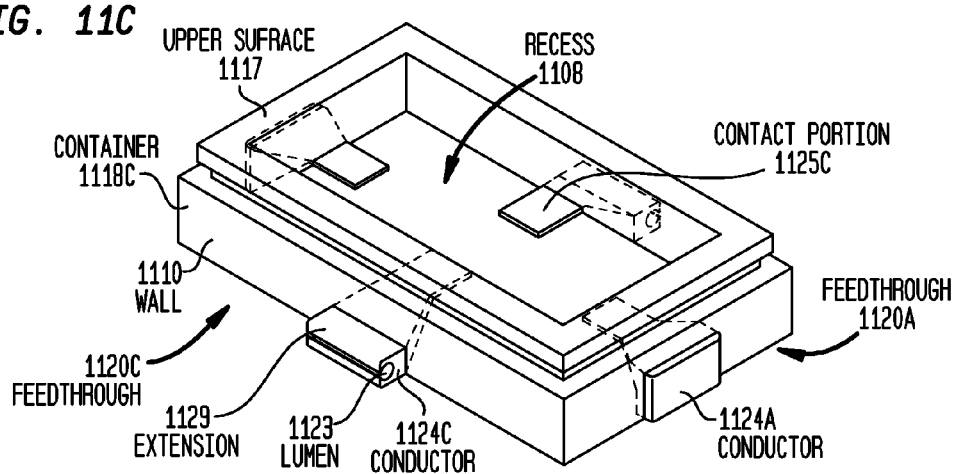
FIG. 11C is a perspective view feedthroughs of another container, wherein the feedthroughs may be formed in accordance with embodiments of the present invention.

FIG. 11C is a perspective view feedthroughs 1120A and 1124C of another container 1118C, wherein the feedthroughs may be formed in accordance with other embodiments of the present invention. As shown in FIG. 11C, container 1118C is similar to container 1118A with feedthroughs 1120A, except that container 1118C includes feedthroughs 1120C instead of feedthroughs 1120A in two of walls 1110 of container 1118C. Feedthroughs 1120C are similar to feedthroughs 1120A, except that conductors 1124C of feedthroughs 1120C have a different shape than conductors 1124A of feedthroughs 1120A. As shown in FIG. 11C, each of conductors 1124C includes an extension 1129 exposed at and extending from a wall 1110 adjacent a bottom surface of container 1118C opposite upper surface 1117. As shown, each of extensions 1129 of conductors 1124C includes a lumen 1123. Container 1118C with feedthroughs 1120A and 1120C may be formed by a process similar to the process described above with reference to FIG. 11A, except that cores 942 may be shaped to form core cavities 928 shaped like conductors 1124A and 1124C.

Figure 12:
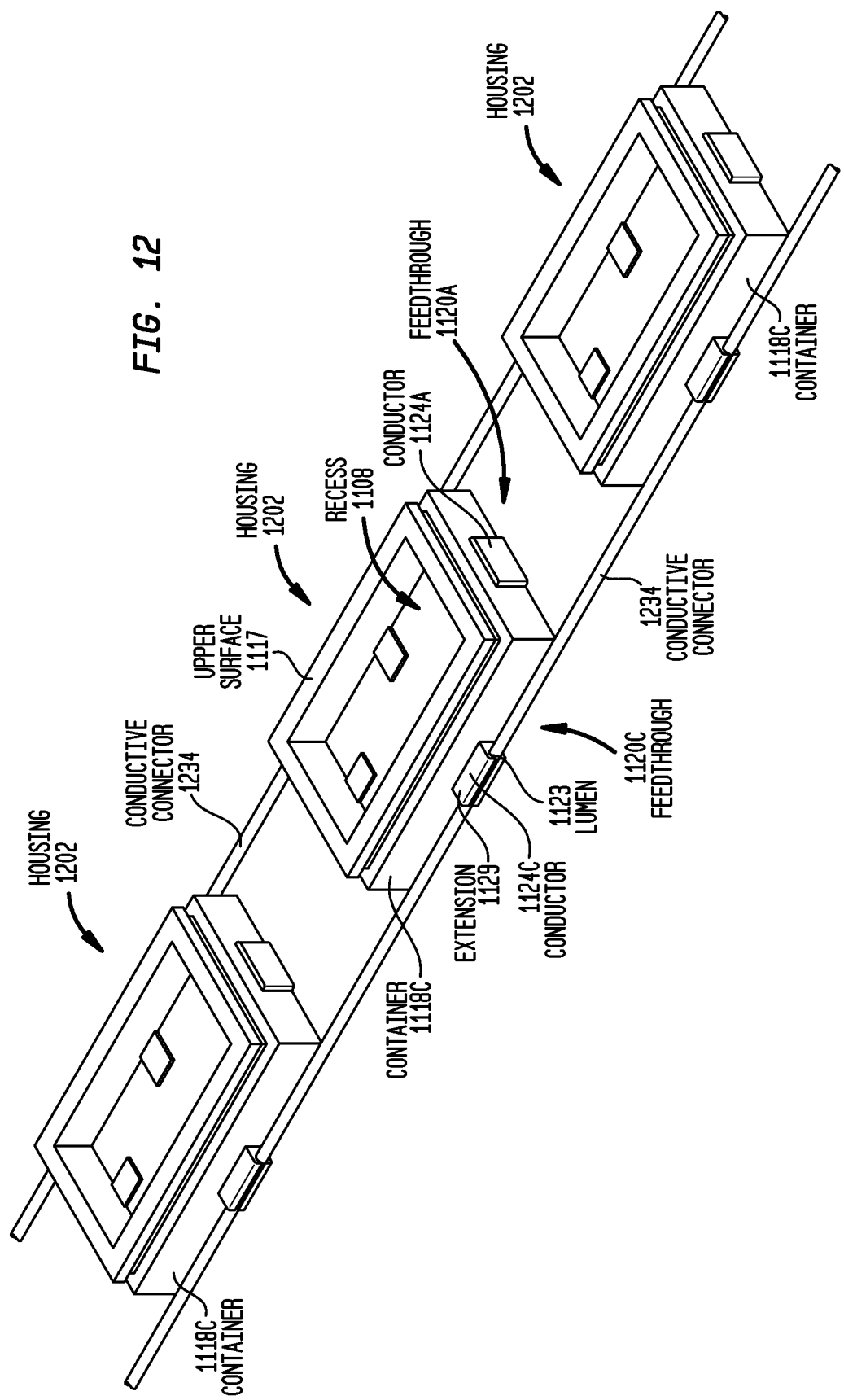
FIG. 12 is a perspective view of a plurality of physically- and electrically-connected housings in accordance with embodiments of the present invention.

FIG. 12 is a perspective view of a plurality of physically- and electrically-connected housings 1202 in accordance with embodiments of the present invention. Functional components and lids of housings 1202 have been omitted for ease of illustration and description. In the embodiment illustrated in FIG. 12, each of housings 1202 includes a container 1118C having feedthroughs 1120A and 1120C, as illustrated in FIG. 11C. As described above with reference to FIG. 11C, each of feedthroughs 1120C comprises a conductor 1124C including an extension 1129 having a lumen 1123. In the embodiment illustrated in FIG. 12, a conductive connector 1234 extends through the lumens 1123 of the conductors 1124C on a first side of each of containers 1118C. In addition, another conductive connector 1234 extends through the lumens 1123 of the conductors 1124C on a second side of each of containers 1118C opposite the respective first sides. In embodiments, each conductive connector 1234 may form an interference fit with conductors 1124 inside lumen 1123. Each of conductive connectors 1234 is a conductor that physically- and electrically-connects a plurality of housings 1202. Conductive connectors 1234 electrically connect housings 1202 by making contact with conductors 1124C within lumens 1123. In certain embodiments, conductive connectors 1234 are rigid, while in other embodiments, conductive connectors 1234 are pliable. In embodiments, each conductive connector 1234 may be a conductive ribbon, rod or wire. Before or after connecting conductors 1124C using conductive connectors 1234, one or more functional components may be mounted recesses 1108 of each container 1118C and electrically connected to conductors 1124A and 1124C as described above with reference to FIGS. 11A-11C. Lids may also be sealed to the upper surface 1117 of each container 1117 to form housings 1202 before or after connecting conductors 1124C using conductive connectors 1234. Physically- and electrically-connected housings 1202 may be used as a multiple-component implant, for example.

FIGS. 13A and 13B are cross-sectional views of a housing 1302 with feedthroughs 1120C that may be formed in accordance with embodiments of the present invention. As shown in FIGS. 13A and 13B, housing 1302 comprises a container 1318 in which feedthroughs 1120C are formed, and a lid 1319 configured to be hermetically sealed to container 1318. In embodiments, container 1318 may be similar to container 1118C of FIG. 11C including feedthroughs 1120A and 1120C, except that container 1318 further includes one or more attachment elements 1382 which are made of a suitable material to facilitate bonding between the two elements. Such material may be metallic in nature or it may be a ceramic loaded with another material (e.g. Ti or TiN) which facilitates a bonding process such as laser welding. As shown, container 1318 includes non-metallic portions 1372 and attachment elements 1382. In certain embodiments, the one or more metallic attachment elements 1382 extend around the entire perimeter of an upper surface 1317 of container 1318. As shown, lid 1319 includes a non-metallic portion 1374 and one or more metallic attachment elements 1384. In certain embodiments, the one or more metallic attachment elements 1384 extend around the entire perimeter of lid 1319. In embodiments of the present invention, non-metallic portions 1372 and 1374 may be formed from non-electrically conductive PIM feedstock and metallic attachment elements 1382 and 1384 may be formed from electrically conductive, metallic PIM feedstock using two-material PIM.

As shown in FIG. 13A, before sealing lid 1319 to container 1318, a functional component 1390 may be mounted inside a recess 1308 of container 1318 and electrically connected to conductors 1124C via wires 1392 or other conductors. Then, as shown in FIG. 13B, lid 1319 may be placed on and sealed to container 1318. In embodiments, lid 1319 may be placed on container 1318 such that metallic attachment elements 1382 of container 1318 make contact with metallic attachment elements 1384 of lid 1319. In such embodiments, metallic attachment elements 1382 may be joined to 1384 by any suitable bonding process such as welding, brazing, soldering, etc. Bonding metallic portions of the container and lid may improve the hermetic seal of housing 1302.

Container 1318 with feedthroughs 1120A and 1120C may be formed by a process similar to the process described above with reference to FIG. 11C, except that additional cores 942, shaped like attachment elements 1382, may be disposed in mold cavity 956 when the non-electrically conductive PIM feedstock is injected in order to form additional core cavities 928 in mold cavity 956. As such, after removing all cores 942, core cavities 928 shaped like attachment elements 1382 will be present in mold cavity 956, in addition to core cavities 928 in which conductors 1124A and 1124C will be formed. After removing all of the cores, a metallic, electrically conductive PIM feedstock is injected into the core cavities to form conductors 1124A and 1124C, and attachment elements 1382. Container 1318 and conductors 1124A and 1124C are then subjected to debinding and sintering processes, as described above. Additionally, in embodiments of the present invention, lid 1319 may be formed by a similar two-material PIM process. For example, in embodiments, lid 1319 may be formed in accordance with the process described above with reference to FIGS. 9A-9E.

In such embodiments, mold cavity 956 is shaped to form non-metallic portion 1374 of lid 1319 when the non-electrically conductive PIM feedstock is injected into mold cavity 956. Single- or multi-piece cores 942 having the shape of metallic attachment elements 1384 are disposed in mold cavity 956 when the non-electrically conductive PIM feedstock is injected in order to form core cavities 928 shaped like attachment elements 1384 in mold cavity 956. After removing cores 942, metallic, electrically conductive PIM feedstock is injected into the core cavities to form metallic attachment elements 1384 on the periphery of lid 1319, as shown in FIG. 13A. Lid 1319 may then be removed from the mold and subjected to debinding and sintering processes, as described above. In certain embodiments, lid 1319 is formed at the same time as container 1318 and conductors 1124, with lid 1319 and container 1318 being formed in different mold cavities 956 of the same mold 950.

In addition, when PIM processes described herein in accordance with embodiments of the present invention are used to form a housing 1302, additional features may be included in housing 1302 at little or no additional cost. For example, in certain embodiments, lid 1319 may be formed to have a thin central region 1386 between side regions 1388 that are thicker than central region 1386, as shown in FIG. 13A. After sealing lid 1319 to container 1318, thin central region 1386 may be used to determine whether a hermetic seal has been achieved between container 1318 and lid 1319. In certain embodiments, thin central region 1386 may be thin enough that a change in ambient pressure deflects central region 1386 enough that the deflection may be measured by a suitable apparatus, such as an interferometer. Once the ambient pressure has been changed, central region 1386 will remain deflected over time if housing 1302 has been hermetically sealed. However, if housing 1302 has not been hermetically sealed, then the pressure inside housing 1302 will equalize with the pressure outside of housing 1302, and the deflection of central region 1386 will decrease partially or completely. By varying the shape of a mold cavity 956 in which lid 1319 is formed, lid 1319 may be formed with either a central region 1386 that is thinner than side regions 1388, or with a central region 1386 that is the same thickness as side regions 1388.

In other embodiments of the present invention, the process of forming housing 1302 may be modified to form additional conductors on lid 1319 for use in determining whether housing 1302 has been hermetically sealed. In certain embodiments, for example, additional cores may be used in the mold cavity during a two-material PIM process to form a first lid cavity extending across an outer surface of lid 1319 having a first thickness that will not be deflected by a change in ambient pressure, and a second lid cavity extending across an outer surface of lid 1319 having a second thickness thinner than the first thickness and thin enough to be deflected by a change in ambient pressure. In embodiments, the first and second lid cavities have the same length, and two conductors of equal length and relative small cross-sectional area may then be formed in the lid cavities when the electrically conductive PIM feedstock is injected into the mold, as described above. The two conductors may then be used as a strain gauge to determine whether housing 1302 has been hermetically sealed. In certain embodiments, the two conductors are used as two arms of a Wheatstone bridge to detect whether the thinner portion of the lid remains deflected after a change in ambient pressure. When the ambient pressure is changed such that the thinner portion of the lid is deflected, the resistance of the conductor extending across the thinner portion will change. Whether the thinner section remains deflected over time, or returns to an equilibrium state, may then be monitored by monitoring the resistance of the conductor extending over the thin section of the lid in comparison to the resistance of the other conductor. As described above, if the thin section remains deflected over time, then a hermetic seal has been achieved. As such, the resistance of the conductors may be monitored in order to test the hermetic seal of housing 1302 without the need for expensive interferometric measurement equipment.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. The present embodiments are, therefore, to be considered in all respects as illustrative and not restrictive.

What is claimed is:

1. A method of forming a feedthrough using a mold that defines a cavity when closed, the mold including one or more cores configured to move in and out of the mold cavity, the method comprising:
injecting non-electrically conductive powder injection molding (PIM) feedstock into the mold cavity to form an insulative body around a portion of each of the cores disposed in the mold cavity;
removing each of the cores from the insulative body to form one or more core cavities in the insulative body;
injecting electrically conductive PIM feedstock into the core cavities to form one or more conductors in the core cavities, respectively; and
sintering the insulative body and the conductors to form the feedthrough.

2. The method of claim 1, further comprising:
integrating the feedthrough into a first wall of a container such that an interface between the feedthrough and the wall is hermetically sealed, wherein the container comprises a plurality of walls defining a recess.

3. The method of claim 2, wherein the one or more conductors are exposed on first and second sides of the first wall.

4. The method of claim 3, further comprising:
mounting at least one functional component in the recess; and
electrically connecting the functional component to at least one of the conductors.

5. The method of claim 1, wherein the diameter of at least one of the conductors varies along the length of the conductor.

6. The method of claim 1, wherein at least one of the conductors has a central region disposed between first and second ends, wherein the diameter of the central region is smaller than the respective diameters of the first and second ends.

7. The method of claim 1, further comprising:
heating the non-electrically conductive feedstock prior to injecting the non-electrically conductive feedstock into the mold cavity; and
heating the electrically conductive feedstock prior to injecting the electrically conductive feedstock into the core cavities.

8. A method of forming an implantable device comprising a feedthrough using a mold that defines a cavity when closed and including one or more cores configured to move in and out of the mold cavity, the method comprising:
injecting non-electrically conductive powder injection molding (PIM) feedstock into the mold cavity to form a container at least partially around the cores disposed in the mold cavity;
removing the cores from the container to form one or more core cavities;
injecting electrically conductive PIM feedstock into the core cavities to form one or more conductors in the core cavities, respectively, each conductor having a first end exposed in a recess of the container and a second end exposed adjacent an outer surface of the container;
sintering the container and the conductors; and
hermetically sealing a lid to the container to form a first housing.

9. The method of claim 8, further comprising:
mounting at least one functional component in the recess; and
electrically connecting the functional component to at least one of the conductors.

10. The method of claim 8, further comprising:
connecting at least one of the conductors of the first housing to at least one conductor of a second housing via an electrical connector to physically and electrically connect the first and second housings.

11. The method of claim 10, wherein the at least one of the conductors of the first housing comprises a first lumen configured to receive the electrical connector such that an interference fit is formed between the electrical connector and the at least one of the conductors.

12. The method of claim 8, wherein a first one of the conductors extends through a first wall of the container and a second one of the conductors extends through a second wall of the container.

13. The method of claim 12, wherein the first and second conductors have different shapes.

14. The method of claim 8, further comprising:
heating the non-electrically conductive feedstock prior to injecting the non-electrically conductive feedstock into the mold cavity; and
heating the electrically conductive feedstock prior to injecting the electrically conductive feedstock into the core cavities.

15. A method of forming a hermetically sealed housing comprising a feedthrough using a mold that defines a first mold cavity when closed and includes a plurality of first cores configured to move in and out of the first mold cavity, the method comprising:
injecting non-electrically conductive powder injection molding (PIM) feedstock into the first mold cavity to form a first insulative body at least partially around the first cores disposed in the first mold cavity;
removing the first cores from the first mold cavity to form a plurality of first core cavities each disposed in or adjacent to the first insulative body;
injecting the heated, electrically conductive metallic PIM feedstock into the first core cavities to form a first container having one or more conductors and one or more first metallic attachment elements, wherein each of the one or more conductors has a first end exposed in a recess of the first insulative body and a second end exposed adjacent an outer surface of the first insulative body;
sintering the container; and
joining one or more second metallic attachment elements of a lid to the first metallic attachment elements, respectively, to form a hermetically sealed housing.

16. The method of claim 15, further comprising:
injecting the heated, non-electrically conductive feedstock into a second mold cavity of the mold to form a second insulative body at least partially around one or more second cores disposed in second mold cavity;
removing the second cores from the second mold cavity to form a plurality of second core cavities each disposed in or adjacent to the second insulative body; and
injecting the heated, electrically conductive feedstock into the second core cavities to form the second container having the one or more second metallic attachment elements.

17. The method of claim 16, wherein the second metallic attachment elements are joined to the first metallic attachment elements via one or more of a welding process, a brazing process, and a soldering process.

18. The method of claim 15, further comprising:
   mounting at least one functional component in the recess; and
   electrically connecting the functional component to at least one of the conductors.

19. The method of claim 15, wherein a first one of the conductors extends through a first wall of the container and a second one of the conductors extends through a second wall of the container.

20. The method of claim 15, further comprising:
   heating the non-electrically conductive feedstock prior to injecting the non-electrically conductive feedstock into the first mold cavity; and
   heating the electrically conductive feedstock prior to injecting the electrically conductive feedstock into the first core cavities.

* * * * *